(12) United States Patent
Aouad et al.

(10) Patent No.: US 10,556,995 B2
(45) Date of Patent: *Feb. 11, 2020

(54) PROCESS FOR MAKING A COMPOSITION COMPRISING BENEFIT AGENT DELIVERY PARTICLES

(71) Applicant: The Procter & Gamble Company, Cincinnati, OH (US)

(72) Inventors: Yousef Georges Aouad, Cincinnati, OH (US); Johan Smets, Lubbeek (BE); Luke Andrew Zannoni, West Chester, OH (US); Piero Baglioni, Fiesole (IT); Paolo Tempesti, Prato (IT); Arianna Bartolini, Florence (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/702,794

(22) Filed: Sep. 13, 2017

(65) Prior Publication Data

US 2018/0072852 A1 Mar. 15, 2018

Related U.S. Application Data

(60) Provisional application No. 62/393,821, filed on Sep. 13, 2016.

(51) Int. Cl.

| C08G 81/02 | (2006.01) |
|---|---|
| A61K 8/02 | (2006.01) |
| A61K 8/91 | (2006.01) |
| A61Q 5/12 | (2006.01) |
| A61Q 19/00 | (2006.01) |
| C11D 3/37 | (2006.01) |
| C11D 3/50 | (2006.01) |
| A61Q 5/02 | (2006.01) |
| C11D 3/42 | (2006.01) |
| C11D 17/00 | (2006.01) |

(52) U.S. Cl.
CPC .......... *C08G 81/025* (2013.01); *A61K 8/0241* (2013.01); *A61K 8/0291* (2013.01); *A61K 8/91* (2013.01); *A61Q 5/02* (2013.01); *A61Q 5/12* (2013.01); *A61Q 19/00* (2013.01); *C11D 3/373* (2013.01); *C11D 3/3788* (2013.01); *C11D 3/42* (2013.01); *C11D 3/505* (2013.01); *C11D 17/0039* (2013.01); *A61K 2800/56* (2013.01)

(58) Field of Classification Search
None
See application file for complete search history.

(56) References Cited

U.S. PATENT DOCUMENTS

| 6,328,988 B1 * | 12/2001 | Uhrich | A61K 9/0014 424/422 |
|---|---|---|---|
| 7,851,543 B2 | 12/2010 | Emrick | |
| 2004/0266655 A1 | 12/2004 | Baum | |
| 2008/0255326 A1 | 10/2008 | Widmaier | |
| 2009/0176935 A1 | 7/2009 | Boeckh et al. | |
| 2010/0204425 A1 | 8/2010 | Mertoglu | |
| 2012/0141796 A1 | 6/2012 | Adamson et al. | |
| 2013/0150277 A1 | 6/2013 | Fischer | |
| 2014/0065234 A1 | 3/2014 | Shum et al. | |
| 2015/0038394 A1 | 2/2015 | Tantawy | |
| 2016/0362644 A1 | 12/2016 | Meine | |
| 2018/0305636 A1 | 10/2018 | Kolter | |

FOREIGN PATENT DOCUMENTS

| EP | 2334776 B1 | 8/2010 |
|---|---|---|
| EP | 3126478 B1 | 9/2018 |
| WO | WO2007/051743 A2 | 5/2007 |
| WO | WO2009013202 A1 | 1/2009 |

OTHER PUBLICATIONS

Bartolini, "Encapsulation of small molecules by poly(ethylene glycol)-graft-poly(vinyl acetate) unimer micelles", Jun. 1, 2016, https://ecis2016.org/sites/default/files/abstracts/Bartolini.pdf.
Bin Li et al., "A novel amphiphilic copolymer poly(ethylene oxide-co-allyl glucide l ether)-graft-poly([epsilon]-caprolactone): synthesis, self-assembly, and protein encapsulation behavior", Polymer Chemistry, vol. 3, No. 9, Jan. 1, 2012, pp. 2421-2429.
Bradley, "Chemistry at the polymer-particle interface for the design of innovative materials", Soft Matter, 2012, 8, pp. 1268-1274.
International Search Report and Written Opinion dated Nov. 23, 2017, U.S. Appl. No. 15/702,794, 10 pgs.
International Search Report and Written Opinion dated Nov. 23, 2017, U.S. Appl. No. 15/702,801, 12 pgs.
VanHecke, "Jamming of Soft Particles: Geometry, Mechanics, Scaling and isostaticity", arXiv:0911.1384v1 Nov. 7, 2009, 25 pgs.
Yow et al., "Formation of liquid core—polymer shell microcapsules", Soft Matter, 2006, 2, pp. 940-949.
U.S. Appl. No. 15/702,801, filed Sep. 13, 2017, Yousef Georges Aouad et al.
Bartolini, Arianna et al.; Poly(ethylene glycol)-graft-poly(vinyl acetate) single-chain nanoparticles for the encapsulation of small molecules; Phys. Chem. Chem. Phys.; Jan. 17, 2017; vol. 19; pp. 4553-4559.
Polymersomes by Microfluidics; Douglas Adamson—Princeton University; adamson@princeton.edu; https://engineering.princeton.edu/news/2007/03/02/innovation-forum-highlights-rich-range-research ; posted Mar. 2, 2007; downloaded Oct. 4, 2019.

* cited by examiner

*Primary Examiner* — Nicole P Babson
(74) *Attorney, Agent, or Firm* — Gregory S. Darley-Emerson

(57) ABSTRACT

A process of making compositions comprising benefit agent delivery particles comprises the steps of combining a graft co-polymer and a benefit agent to form a premix composition, and combining the premix composition and water and/or consumer product adjunct material to form the compositions. The resulting compositions comprise benefit agent delivery particles that comprise the graft co-polymer and benefit agent.

29 Claims, 1 Drawing Sheet

PROCESS FOR MAKING A COMPOSITION COMPRISING BENEFIT AGENT DELIVERY PARTICLES

FIELD OF THE INVENTION

The present invention relates to processes for making feedstock compositions or consumer product compositions, which comprise benefit agent delivery particles, and products resulting from such processes.

BACKGROUND OF THE INVENTION

Benefit agents, such as perfumes, silicones, waxes, flavors, vitamins and fabric softening agents, are expensive and/or can react with other active ingredients in the composition, for example, personal care compositions, cleaning compositions, and fabric care compositions. As a result, there is a desire to maximize the stability in the final composition of such benefit agents. One method of achieving such objective is to improve the delivery efficiencies of such benefit agents by encapsulating such benefit agents. Unfortunately, encapsulation processes are time consuming and expensive as they typically require chemical reactions such as extensive crosslinking and/or result in capsules that over protect the benefit agent as such capsules typically require a high energy input to release their active—for example pressure, temperature and/or electromagnetic radiation. Furthermore, such encapsulates' shell typically only protects the benefit agent and, on its own, provides no active value and can even be a negative as such encapsulate's cross-linked shell may leave a residue when a product containing the encapsulate is used.

Thus, it has been desired to provide benefit agent-containing delivery particles that can be formed without a crosslinking reaction, which release their benefit agent via the simple dilution of the product matrix in which the particles are contained. It can also be desired to provide a treatment benefit in addition and/or supplementary to the benefit provided by the benefit agent containing delivery particles' benefit agent. What is furthermore desired is using the same polymeric materials to deliver a wide variety of actives with different chemical and physical properties. Furthermore, a tunable delivery particle depending on the delivery needs, whereby specific polymeric delivery materials can be tuned into different delivery systems by the dictation of the specific environmental factors like water content, adjuncts types and levels, and the use of hydrophilic materials. What is furthermore desired is a particle which forms spontaneously when little energy is provided to the system, as for low shear mixing needed to ensure homogeneous distribution of the benefit agent particle within the composition.

SUMMARY OF THE INVENTION

The present invention relates to processes of making compositions comprising benefit agent delivery particles comprises the steps of combining a graft co-polymer and a benefit agent to form a premix composition, and combining the premix composition and water and/or consumer product adjunct material to form the compositions. The resulting compositions comprise benefit agent delivery particles that comprise the graft co-polymer and benefit agent.

The present invention further encompasses a process for making a feedstock composition comprising benefit agent delivery particles comprising the steps of combining a graft co-polymer and a benefit agent to form a premix composition, and combining the premix composition and water to form the feedstock composition. The feedstock composition comprises less than about 98%, by weight of the feedstock composition, of water. The benefit agent delivery particles in the feedstock compositions comprise the graft co-polymer and benefit agent.

The present invention further encompasses a process of making a consumer product composition comprising benefit agent delivery particles comprising the step of combining the feedstock composition comprising benefit agent delivery particles (such as those obtainable by the process of making feedstock compositions of the present invention) and consumer product adjunct material to form the consumer product composition.

The present invention further encompasses a process of making a consumer product composition comprising benefit agent delivery particles comprising the steps of combining a graft co-polymer and a benefit agent to form a premix composition, and combining said premix composition and consumer product adjunct material to form said consumer product composition. The consumer product adjunct material is preferably selected from the group consisting of enzymes, bleaching agents silicones, perfumes, fabric hueing agents, and mixtures thereof.

The present invention further encompasses compositions obtainable by (i.e. produced according to) the processes of the present invention, including feedstock compositions obtainable by the processes of the present invention and consumer product compositions obtainable by the processes of the present invention.

DETAILED DESCRIPTION OF THE INVENTION

Definitions

As used herein "consumer product" means baby care, beauty care, fabric & home care, family care, feminine care, health care, snack and/or beverage products or devices intended to be used or consumed in the form in which it is sold, and not intended for subsequent commercial manufacture or modification. Such products include but are not limited to fine fragrance (e.g. perfumes, colognes eau de toilettes, after-shave lotions, pre-shave, face waters, tonics, and other fragrance-containing compositions for application directly to the skin), diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, tooth whitening; over-the-counter health care including cough and cold remedies, pain relievers, RX pharmaceuticals, pet health and nutrition, and water purification; processed food products intended primarily for consumption between customary meals or as a meal accompaniment (non-limiting examples include potato chips, tortilla chips, popcorn, pretzels, corn chips, cereal bars, vegetable chips or crisps, snack mixes, party mixes, multigrain chips, snack crackers, cheese snacks, pork rinds, corn snacks, pellet snacks, extruded snacks and bagel chips); and coffee.

As used herein, the term "cleaning composition" includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various pouches, tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners; hair shampoos and hair-rinses; shower gels and foam baths and metal cleaners; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists.

As used herein, the term "fabric care composition" includes, unless otherwise indicated, fabric softening compositions, fabric enhancing compositions, fabric freshening compositions and combinations thereof. The form of such compositions includes liquids, gels, beads, powders, flakes, and granules.

As used herein the term "unit dose article" means powder or solid detergent in a water soluble film.

The test methods disclosed in the Test Methods Section of the present application should be used to determine the respective values of the parameters of Applicants' inventions.

Processes of Making Compositions Comprising Benefit Agent Delivery Particles

The present invention relates to processes of making compositions comprising benefit agent delivery particles, wherein the benefit agent delivery particles comprise a graft co-polymer and benefit agent. The graft co-polymer and benefit agent are premixed, preferably with water, to form benefit agent particles in the compositions. Such compositions can be feedstock compositions comprising benefit agent delivery particles, wherein such feedstock compositions can be later further combined with consumer product adjunct materials to form consumer product compositions. Such feedstock compositions can therefore be produced, stored, shipped to another manufacturing location to be further combined with consumer product adjunct materials in a separate process to form the consumer product compositions.

In one aspect, the feedstock composition of the present invention is substantially free of consumer product adjunct material. As used herein, "substantially free" means that consumer product adjunct material is not purposely added to the feedstock composition and only trace amounts, if any, of consumer product adjunct material is present in the feedstock composition.

The compositions of the present invention produced by the present processes can further include consumer product compositions, wherein the graft co-polymer and benefit agent premix (with or without water) can be further combined with consumer product adjunct material(s) in the same process to form the consumer product compositions. Such consumer product compositions can therefore be produce in the same process, e.g. the same manufacturing line, in which the graft co-polymer and benefit agent premix is formed.

The step of premixing the graft co-polymer and benefit agent is preferably achieved by mixing the graft co-polymer and benefit agent in a mixing device at a rate of from about 500 to about 3000 rpm, preferably from about 600 to about 2500 rpm, and more preferably about 2500 rpm.

Figure 1:
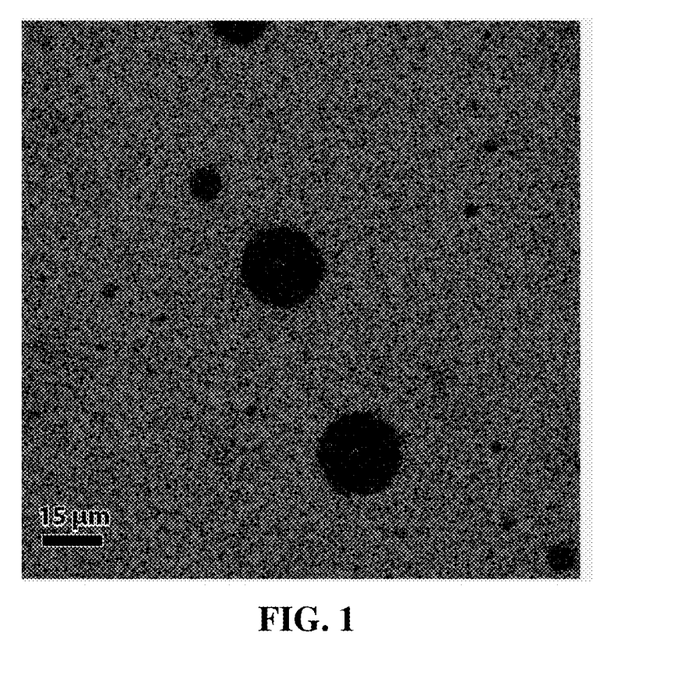
FIG. 1 is a photomicrograph produced using Confocal Laser Scanning Fluorescence Microscopy (CLSM) showing a comparative consumer product composition produced by a conventional process.
Figure 2:
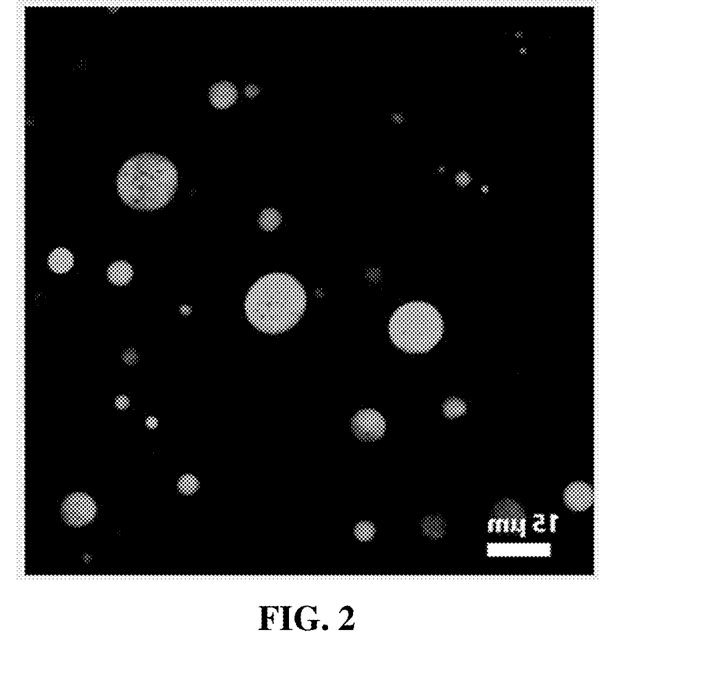
FIG. 2 is a photomicrograph produced using Confocal Laser Scanning Fluorescence Microscopy (CLSM) showing a consumer product composition of the present invention produced by a process of the present invention.

It has been found that premixing the graft co-polymer and benefit agent drives the formation of benefit agent delivery particles, which comprise the graft co-polymer and benefit agent, in the resulting compositions. In contrast, it has been found that separately adding graft co-polymer and benefit agent to a consumer product composition does not result in the formation of benefit agent delivery particles which comprise graft co-polymer and benefit agent. This important difference is illustrated in FIGS. 1 and 2, and described in the Examples section hereinbelow.

Such benefit agent delivery particles can provide benefits such as protecting the materials of the particles from other materials in the compositions, protecting materials in the compositions from the materials of the particles, and/or enhancing the delivery (or deposition) of the benefit agent to the targeted surfaces treated with the compositions.

The present invention further encompasses feedstock compositions and consumer product compositions produced according to the processes of the present invention.

Graft Co-Polymer

A graft copolymer molecule consists of a polymeric main chain, constituted of a long sequence of one monomer (the backbone), on which one or more polymeric side chains, constituted of monomers of a different chemical nature than the backbone, are attached. In graft copolymers a large number of parameters can be varied: the chemical nature, the molecular weight and the molecular weight distribution (MWD) of both the backbone and of the grafts, and the graft density along the backbone. Therefore, graft copolymers represent materials combining the properties of two or more polymers in one entity. Provided appropriate polymerization methods are used, tailor-made graft copolymers can be obtained. In common graft copolymers, the branches are randomly distributed along the backbone. The backbone and the branches may be homo- or copolymers but they differ in chemical nature or composition. Under the synthetic conditions used herein, the graft copolymer will also contain low levels of backbone homopolymer and side-chain graft homopolymer in addition to the graft copolymer itself.

By varying the nature and ratio of the polymers used in the backbone and in the graft, it is possible to obtain graft co-polymers of different amphiphilicity. Suitable graft copolymers according to the invention are constituted of few long Poly Vinyl Acetate (PVAc) hanging off a Polyethylene (PEG) backbone. The graft co-polymer normally has only few graft points (only 1-3 PVAc grafts per the whole PEG chain, where the PEG chain is about 140 units long) with long PVAc chains.

The graft co-polymer can be a solid or semi-solid at 25° C., and have a melting point of at least about 45° C., at least about 60° C., at least about 70° C., or at least about 80° C. As described above, the graft co-polymer is preferably heated to a temperature above its melting point before combining with the benefit agent. Preferably, in the process of the present invention, the graft co-polymer is heated to a temperature of at least about 45° C., at least about 60° C., at least about 70° C., or at least about 80° C.

Preferred graft co-polymers for use herein include a graft co-polymer comprising a co-polymer of polyalkylene glycol and vinyl acetate having:

a) a weight-average molecular weight of from about 2000 Daltons to about 250,000 Daltons, preferably from about 3000 Daltons to about 100,000 Daltons, more preferably 4,000 Daltons to about 50,000 Daltons, most preferably from about 5,000 to about 20,000 Daltons, and b) a ratio of polyalkylene glycol to vinyl acetate moieties of about 5:1 to about 1:10 preferably from about 3:1 to about 1:8, more preferably from about 2:1 to about 1:6; wherein the polyalkylene glycol is preferably selected from the group consisting of polyethylene glycol, polypropylene glycol, polybutylene glycol and mixtures thereof, and more preferably polyethylene glycol. The weight-average molecular weight is determined according to the Weight-Average Molecular Weight Test Method hereinbelow. The ratio of polyalkylene glycol to vinyl acetate moieties is determined according to the Grafting and Ratio of Polyalkylene Glycol: Vinyl Acetate Test Method hereinbelow.

A preferred graft co-polymer for use herein comprises a co-polymer of polyalkylene glycol and vinyl acetate that comprises a polyalkylene glycol backbone comprising vinyl acetate moieties that are covalently attached to said polyalkylene glycol backbone. Preferably, the polyalkylene glycol comprises polyethylene glycol. Preferred graft co-polymers are polyethylene glycol-graft-polyvinyl acetate ("PEG-g-PVAc") amphiliphic co-polymers.

In one aspect, the graft co-polymer can comprise polyalkylene glycol and at least one monomer selected from the group consisting of vinyl esters, alkyl acrylates, alkyl methacrylates, alkyl acrylamides, alkyl methacrylamides, styrenes, halogenated olefins, and mixtures thereof. Preferably the polyalkylene glycol is polyethylene glycol.

A preferred graft co-polymer for use herein comprises a co-polymer of polyalkylene glycol and vinyl acetate having from 1 to about 10 vinyl acetate grafts per polyalkylene glycol backbone, preferably said co-polymer of polyalkylene glycol and vinyl acetate has from 1 to about 5 vinyl acetate moieties per polyalkylene glycol backbone, more preferably said co-polymer of polyalkylene glycol and vinyl acetate has from about 1 to about 3 vinyl acetate grafts per polyalkylene glycol backbone, most preferably said co-polymer of polyalkylene glycol and vinyl acetate has 1 vinyl acetate graft per polyalkylene glycol backbone. Preferably the polyalkylene glycol comprises polyethylene glycol.

Additional non-limiting examples of graft co-polymers useful herein include amphiphilic graft polymers as described in detail in U.S. Pat. No. 8,519,060. Such amphiphilic graft polymers are based on water-soluble polyalkylene oxides as a graft base and side chains formed by polymerization of a vinyl ester component, said polymers having an average of <1 graft site per 50 alkylene oxide units and mean molar masses (Mw) of from 3,000 to 100,000.

Benefit Agent

Suitable benefit agents include those selected from the group consisting of perfume raw materials, silicone oils, waxes, hydrocarbons, higher fatty acids, essential oils, lipids, skin coolants, vitamins, sunscreens, antioxidants, glycerine, catalysts, bleach particles, silicon dioxide particles, malodor reducing agents, odor-controlling materials, chelating agents, antistatic agents, softening agents, insect and moth repelling agents, colorants, antioxidants, chelants, bodying agents, drape and form control agents, smoothness agents, wrinkle control agents, sanitization agents, disinfecting agents, germ control agents, mold control agents, mildew control agents, antiviral agents, drying agents, stain resistance agents, soil release agents, fabric refreshing agents and freshness extending agents, chlorine bleach odor control agents, dye fixatives, dye transfer inhibitors, color maintenance agents, optical brighteners, color restoration/rejuvenation agents, anti-fading agents, whiteness enhancers, anti-abrasion agents, wear resistance agents, fabric integrity agents, anti-wear agents, anti-pilling agents, defoamers, anti-foaming agents, UV protection agents for fabrics and skin, sun fade inhibitors, anti-allergenic agents, enzymes, water proofing agents, fabric comfort agents, shrinkage resistance agents, stretch resistance agents, stretch recovery agents, skin care agents, glycerin, natural actives, aloe vera, vitamin E, shea butter, cocoa butter, brighteners, antibacterial actives, antiperspirant actives, cationic polymers, dyes, hueing dyes, skin heath agents, skin restoration agents, anti skin aging agents, facial contrast agents, anti dandruff agents, skin lightening agents, anti-acne agents, emollients, non-steroidal anti-inflammatory agents, topical anaesthetics, artificial tanning agents, anti-microbial and anti-fungal actives, skin soothing agents, skin barrier repair agents, anti-skin atrophy actives, lipids, sebum inhibitors, sebum inhibitors, skin sensates, protease inhibitors, anti-itch agents, desquamation enzyme enhancers, anti-glycation agents and mixtures thereof.

Preferred benefit agents for use in forming the benefit agent delivery particles herein are selected from the group consisting of enzymes, bleach systems/bleaching agents, silicones, perfumes, hueing agents, and mixtures thereof. More preferred benefit agents are selected from the group consisting of perfumes, silicones, fabric hueing agents, and mixtures thereof. More preferred benefit agents include neat perfume oil.

Enzymes—The compositions may contain one or more detergent enzymes which provide cleaning performance and/or fabric care benefits. Examples of suitable enzymes include hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, DNases and amylases, or mixtures thereof. A typical combination may be a cocktail of conventional applicable enzymes like protease, lipase, cutinase and/or cellulase in conjunction with amylase.

Bleach system—Bleach systems suitable for use herein contain one or more bleaching agents. Non-limiting examples of suitable bleaching agents include catalytic metal complexes; activated peroxygen sources; bleach activators; bleach boosters; photobleaches; bleaching enzymes; free radical initiators; $H_2O_2$; hypohalite bleaches; peroxygen sources, including perborate and/or percarbonate and combinations thereof. Suitable peroxygen sources include peroxy acids. Typical monoperoxy acids useful herein include alkyl and aryl peroxyacids such as: (i) peroxybenzoic acid and ring-substituted peroxybenzoic acid, e. g. peroxy-α naphthoic acid, monoperoxyphthalic acid (magnesium salt hexahydrate), and o-carboxybenzamidoperoxyhexanoic acid (sodium salt); (ii) aliphatic, substituted aliphatic and arylalkyl monoperoxy acids, e. g. peroxylauric acid, peroxystearic acid, N-nonanoylaminoperoxycaproic acid (NAPCA). N,N-(3-octylsuccinoyl) aminoperoxycaproic acid (SAPA) and N. N-phthaloylaminoperoxycaproic acid (PAP); (iii) amidoperoxyacids, e. g. monononylamide of either peroxysuccinic acid (NAPSA) or of peroxyadipic acid (NAPAA). Typical diperoxyacids useful herein include alkyl diperoxyacids and aryldiperoxyacids, such as: (iv) 1,12-diperoxydodecancdioic acid; (v) 1,9-diperoxyazelaic acid; (vi) diperoxybrassylic acid; diperoxysebacic acid and diperoxyisophthalic acid: (vii) 2-decyldiperoxybutane-1,4-dioic acid; (viii) 4,4'-sulfonylbisperoxybenzoic acid. Suitable bleach activators include perhydrolyzable esters and perhydrolyzable imides such as, tetraacetyl ethylene diamine, octanoylcaprolactam, benzoyloxybenzenesulphonate, nonanoyloxybenzene-sulphonate, benzoylvalerolactam, dodecanoyloxybenzenesulphonate. Other bleaching agents include metal complexes of transitional metals with ligands of defined stability constants.

Silicones—Suitable silicones comprise Si—O moieties and may be selected from (a) non-functionalized siloxane polymers, (b) functionalized siloxane polymers, and combinations thereof. The molecular weight of the organosilicone is usually indicated by the reference to the viscosity of the material. In one aspect, the organosilicones may comprise a viscosity of from about 10 to about 2,000,000 centistokes at 25° C. In another aspect, suitable organosilicones may have a viscosity of from about 10 to about 800,000 centistokes at 25° C.

Suitable organosilicones may be linear, branched or cross-linked.

In one aspect, the organosilicone may comprise a cyclic silicone. The cyclic silicone may comprise a cyclomethicone of the formula $[(CH_3)_2SiO]_n$ where n is an integer that may range from about 3 to about 7, or from about 5 to about 6.

In one aspect, the organosilicone may comprise a functionalized siloxane polymer. Functionalized siloxane polymers may comprise one or more functional moieties selected from the group consisting of amino, amido, alkoxy, hydroxy, polyether, carboxy, hydride, mercapto, sulfate phosphate, and/or quaternary ammonium moieties. These moieties may be attached directly to the siloxane backbone through a bivalent alkylene radical, (i.e., "pendant") or may be part of the backbone. Suitable functionalized siloxane polymers include materials selected from the group consisting of aminosilicones, amidosilicones, silicone polyethers, silicone-urethane polymers, quaternary ABn silicones, amino ABn silicones, and combinations thereof.

In one aspect, the functionalized siloxane polymer may comprise a silicone polyether, also referred to as "dimethicone copolyol." In general, silicone polyethers comprise a polydimethylsiloxane backbone with one or more polyoxyalkylene chains. The polyoxyalkylene moieties may be incorporated in the polymer as pendent chains or as terminal blocks. In another aspect, the functionalized siloxane polymer may comprise an aminosilicone.

In one aspect, the organosilicone may comprise amine ABn silicones and quat ABn silicones. Such organosilicones are generally produced by reacting a diamine with an epoxide.

In another aspect, the functionalized siloxane polymer may comprise silicone-urethanes. These are commercially available from Wacker Silicones under the trade name SLM-21200®.

Perfume—The perfume component may comprise a component selected from the group consisting of:
(1) a neat perfume oil;
(2) a perfume delivery technology;
(3) a pro-perfume;
(4) a low odor detection threshold perfume ingredients, wherein said low odor detection threshold perfume ingredients may comprise less than about 25%, by weight of the total neat perfume composition; and
(5) mixtures thereof.

In a preferred aspect, the benefit agent of the benefit agent delivery particles herein is a neat perfume oil.

In one aspect, the following perfume delivery technologies (PDTs) may be used, such as polymer assisted delivery, matrix systems, reservoir systems, amine assisted delivery, and/or zeolite and inorganic carriers. Such perfume delivery technologies can be utilized as a benefit agent in combination with the graft co-polymer herein to form benefit agent delivery particles.

Polymer Assisted Delivery (PAD): This perfume delivery technology uses polymeric materials to deliver perfume materials, wherein such polymeric materials are not graft co-polymers. Classical coacervation, water soluble or partly soluble to insoluble charged or neutral polymers, liquid crystals, hot melts, hydrogels, perfumed plastics, microcapsules, nano- and micro-latexes, polymeric film formers, and polymeric absorbents, polymeric adsorbents. etc. are some examples. PAD includes but is not limited to:

Matrix Systems: The fragrance is dissolved or dispersed in a polymer matrix or particle. Absorption and/or adsorption into or onto polymeric particles, films, solutions, and the like are aspects of this technology. Nano- or micro-particles composed of organic materials (e.g., latexes) are examples. Suitable particles include a wide range of materials including, but not limited to polyacetal, polyacrylate, polyacrylic, polyacrylonitrile, polyamide, polyaryletherketone, polybutadiene, polybutylene, polybutylene terephthalate, polychloroprene, poly ethylene, polyethylene terephthalate, polycyclohexylene dimethylene terephthalate, polycarbonate, polychloroprene, polyhydroxyalkanoate, polyketone, polyester, polyethylene, polyetherimide, polyethersulfone, polyethylenechlorinates, polyimide, polyisoprene, polylactic acid, polymethylpentene, polyphenylene oxide, polyphenylene sulfide, polyphthalamide, polypropylene, polystyrene, polysulfone, polyvinyl acetate, polyvinyl chloride, aminoplast, as well as polymers or copolymers based on acrylonitrile-butadiene, cellulose acetate, ethylene-vinyl acetate, ethylene vinyl alcohol, styrene-butadiene, vinyl acetate-ethylene, and mixtures thereof.

Reservoir Systems: Reservoir systems are also known as a core-shell type technology, or one in which the fragrance is surrounded by a perfume release controlling membrane, which may serve as a protective shell. The material inside the microcapsule is referred to as the core, internal phase, or fill, whereas the wall is sometimes called a shell, coating, or membrane. Microparticles or pressure sensitive capsules or microcapsules are examples of this technology. Microcapsules of the current invention are formed by a variety of procedures that include, but are not limited to, coating, extrusion, spray-drying, interfacial, in-situ and matrix polymerization. The possible shell materials vary widely in their stability toward water. Among the most stable are polyoxymethyleneurea (PMU)-based materials, which may hold certain PRMs for even long periods of time in aqueous solution (or product). Such systems include but are not limited to urea-formaldehyde and/or melamine-formaldehyde. Gelatin-based microcapsules may be prepared so that they dissolve quickly or slowly in water, depending for example on the degree of cross-linking. Many other capsule wall materials are available and vary in the degree of perfume diffusion stability observed. Without wishing to be bound by theory, the rate of release of perfume from a capsule, for example, once deposited on a surface is typically in reverse order of in-product perfume diffusion stability.

Molecule-Assisted Delivery (MAD): Non-polymer materials or molecules may also serve to improve the delivery of perfume. Without wishing to be bound by theory, perfume may non-covalently interact with organic materials, resulting in altered deposition and/or release. Non-limiting examples of such organic materials include but are not limited to hydrophobic materials such as organic oils, waxes, mineral oils, petrolatum, fatty acids or esters, sugars, surfactants, liposomes and even other perfume raw material (perfume oils), as well as natural oils, including body and/or other soils. Perfume fixatives are yet another example. In one aspect, non-polymeric materials or molecules have a C Log P greater than about 2.

Amine Assisted Delivery (AAD): The amine-assisted delivery technology approach utilizes materials that contain an amine group to increase perfume deposition or modify perfume release during product use. There is no requirement in this approach to pre-complex or pre-react the perfume raw material(s) and amine prior to addition to the product. In one aspect, amine-containing AAD materials suitable for use herein may be non-aromatic; for example, polyalkylimine, such as polyethyleneimine (PEI), or polyvinylamine (PVAm), or aromatic, for example, anthranilates. Such materials may also be polymeric or non-polymeric. In one aspect, such materials contain at least one primary amine. This technology will allow increased longevity and controlled release also of low ODT perfume notes (e.g., aldehydes, ketones, enones) via amine functionality, and delivery of other PRMs, without being bound by theory, via polymer-assisted delivery for polymeric amines.

Zeolite & Inorganic Carrier (ZIC): This technology relates to the use of porous zeolites or other inorganic materials to deliver perfumes.

Pro-Perfume (PP): This technology refers to perfume technologies that result from the reaction of perfume materials with other substrates or chemicals to form materials that have a covalent bond between one or more PRMs and one or more carriers. The PRM is converted into a new material called a pro-PRM (i.e., pro-perfume), which then may release the original PRM upon exposure to a trigger such as water or light. Pro-perfumes may provide enhanced perfume delivery properties such as increased perfume deposition, longevity, stability, retention, and the like. Pro-perfumes include those that are monomeric (non-polymeric) or polymeric, and may be pre-formed or may be formed in-situ under equilibrium conditions, such as those that may be present during in-product storage or on the wet or dry situs. Nonlimiting examples of pro-perfumes include Michael adducts (e.g., beta-amino ketones), aromatic or non-aromatic imines (Schiff bases), oxazolidines, beta-keto esters, and orthoesters. Another aspect includes compounds comprising one or more beta-oxy or beta-thio carbonyl moieties capable of releasing a PRM, for example, an alpha, beta-unsaturated ketone, aldehyde or carboxylic ester.

Fabric Hueing Agents—The composition may comprise a fabric hueing agent (sometimes referred to as shading, blueing or whitening agents). Typically the hueing agent provides a blue or violet shade to fabric. Hueing agents can be used either alone or in combination to create a specific shade of hueing and/or to shade different fabric types. This may be provided for example by mixing a red and green-blue dye to yield a blue or violet shade. Hueing agents may be selected from any known chemical class of dye, including but not limited to acridine, anthraquinone (including polycyclic quinones), azine, azo (e.g., monoazo, disazo, trisazo, tetrakisazo, polyazo), including premetallized azo, benzodifurane and benzodifuranone, carotenoid, coumarin, cyanine, diazahemicyanine, diphenylmethane, formazan, hemicyanine, indigoids, methane, naphthalimides, naphthoquinone, nitro and nitroso, oxazine, phthalocyanine, pyrazoles, stilbene, styryl, triarylmethane, triphenylmethane, xanthenes and mixtures thereof.

Suitable fabric hueing agents include dyes, dye-clay conjugates, and organic and inorganic pigments. Suitable dyes include small molecule dyes and polymeric dyes. Suitable small molecule dyes include small molecule dyes selected from the group consisting of dyes falling into the Colour Index (C.I.) classifications of Acid, Direct, Basic, Reactive (or hydrolysed forms thereof), Solvent or Disperse dyes for example that are classified as Blue, Violet, Red, Green or Black, and provide the desired shade either alone or in combination. In another aspect, suitable small molecule dyes include small molecule dyes selected from the group consisting of Colour Index (Society of Dyers and Colourists, Bradford, UK) numbers Direct Violet dyes such as 9, 35, 48, 51, 66, and 99, Direct Blue dyes such as 1, 71, 80 and 279, Acid Red dyes such as 17, 73, 52, 88 and 150, Acid Violet dyes such as 15, 17, 24, 43, 49 and 50, Acid Blue dyes such as 15, 17, 25, 29, 40, 45, 75, 80, 83, 90 and 113, Acid Black dyes such as 1, Basic Violet dyes such as 1, 3, 4, 10 and 35, Basic Blue dyes such as 3, 16, 22, 47, 66, 75 and 159, Disperse or Solvent dyes as disclosed in U.S. Pat. No. 8,268,016 B2, or dyes as disclosed in U.S. Pat. No. 7,208,459 B2, or dyes disclosed in U.S. Pat. No. 8,247,364 B2 and mixtures thereof. In another aspect, suitable small molecule dyes include small molecule dyes selected from the group consisting of C. I. numbers Acid Violet 17, Acid Blue 80, Acid Violet 50, Direct Blue 71, Direct Violet 51, Direct Blue 1, Acid Red 88, Acid Red 150, Acid Blue 29, Acid Blue 113, fabric hueing agents that undergo a transition on storage or during or after use that either (1) changes the extinction coefficient in the visible range at a set wavelength (400-750 nm) from less than 1000 $M^{-1}$ $cm^{-1}$ to one greater than 5,000, preferably greater than 10,000, more preferably greater than 20,000, even more preferably greater than 50,000, most preferably greater than 80,000 or even 100,000 $M^{-1}$ $cm^{-1}$, (2) increases the extinction coefficient in the visible range at a set wavelength (400-750 nm) by a factor of at least five, preferably ten or even twenty fold wherein the final extinction coefficient at the set wavelength is at least 10,000 $M^{-1}$ $cm^{-1}$, or (3) shifts the wavelength of the maximum extinction coefficient within the visible range from the pre-transition value by at least 25 nm, preferably 50 nm, even more preferably 75 nm, most preferably by 100 nm or more, wherein the final wavelength of the maximum extinction coefficient within the visible range is from about 550 to 700 nm, preferably from 550 to 650 nm, and/or mixtures thereof.

Suitable polymeric dyes include polymeric dyes selected from the group consisting of polymers containing covalently bound (sometimes referred to as conjugated) chromogens, (dye-polymer conjugates), for example polymers with chromogens co-polymerized into the backbone of the polymer and mixtures thereof. Polymeric dyes include those described in U.S. Pat. No. 7,686,892 B2.

In another aspect, suitable polymeric dyes include polymeric dyes selected from the group consisting of fabric-substantive colorants sold under the name of Liquitint® (Milliken, Spartanburg, S.C., USA), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. In still another aspect, suitable polymeric dyes include polymeric dyes selected from the group consisting of Liquitint® Violet CT, carboxymethyl cellulose (CMC) covalently bound to a reactive blue, reactive violet or reactive red dye such as CMC conjugated with C.I. Reactive Blue 19, sold by Megazyme, Wicklow, Ireland under the product name AZO-CM-CELLULOSE, product code S-ACMC, alkoxylated triphenylmethane polymeric colourants, alkoxylated thiophene polymeric colourants, and mixtures thereof.

Suitable dye clay conjugates include dye clay conjugates selected from the group comprising at least one cationic/basic dye and a smectite clay, and mixtures thereof. In another aspect, suitable dye clay conjugates include dye clay conjugates selected from the group consisting of one cationic/basic dye selected from the group consisting of C.I. Basic Yellow 1 through 108, C.I. Basic Orange 1 through 69, C.I. Basic Red 1 through 118, C.I. Basic Violet 1 through 51, C.I. Basic Blue 1 through 164, C.I. Basic Green 1 through 14, C.I. Basic Brown 1 through 23, CI Basic Black 1 through 11, and a clay selected from the group consisting of Montmorillonite clay, Hectorite clay, Saponite clay and mixtures thereof. In still another aspect, suitable dye clay conjugates include dye clay conjugates selected from the group consisting of: Montmorillonite Basic Blue B7 C.I. 42595 conjugate, Montmorillonite Basic Blue B9 C.I. 52015 conjugate, Montmorillonite Basic Violet V3 C.I. 42555 conjugate, Montmorillonite Basic Green G1 C.I. 42040 conjugate, Montmorillonite Basic Red R1 C.I. 45160 conjugate, Montmorillonite C.I. Basic Black 2 conjugate, Hectorite Basic Blue B7 C.I. 42595 conjugate, Hectorite Basic Blue B9 C.I. 52015 conjugate, Hectorite Basic Violet V3 C.I. 42555 conjugate, Hectorite Basic Green G1 C.I. 42040 conjugate, Hectorite Basic Red R1 C.I. 45160 conjugate, Hectorite C.I. Basic Black 2 conjugate, Saponite Basic Blue B7 C.I. 42595 conjugate, Saponite Basic Blue B9 C.I. 52015 conjugate, Saponite Basic Violet V3 C.I. 42555 conjugate, Saponite Basic Green G1 C.I. 42040 conjugate, Saponite Basic Red R1 C.I. 45160 conjugate, Saponite C.I. Basic Black 2 conjugate and mixtures thereof.

The hueing agent may be incorporated into the detergent composition as part of a reaction mixture which is the result of the organic synthesis for a dye molecule, with optional purification step(s). Such reaction mixtures generally comprise the dye molecule itself and in addition may comprise un-reacted starting materials and/or by-products of the organic synthesis route.

Suitable polymeric bluing agents may be alkoxylated. As with all such alkoxylated compounds, the organic synthesis may produce a mixture of molecules having different degrees of alkoxylation. Such mixtures may be used directly to provide the hueing agent, or may undergo a purification step to increase the proportion of the target molecule.

Suitable pigments include pigments selected from the group consisting of flavanthrone, indanthrone, chlorinated indanthrone containing from 1 to 4 chlorine atoms, pyranthrone, dichloropyranthrone, monobromodichloropyranthrone, dibromodichloropyranthrone, tetrabromopyranthrone, perylene-3,4,9,10-tetracarboxylic acid diimide, wherein the imide groups may be unsubstituted or substituted by $C_1$-$C_3$-alkyl or a phenyl or heterocyclic radical, and wherein the phenyl and heterocyclic radicals may additionally carry substituents which do not confer solubility in water, anthrapyrimidinecarboxylic acid amides, violanthrone, isoviolanthrone, dioxazine pigments, copper phthalocyanine which may contain up to 2 chlorine atoms per molecule, polychloro-copper phthalocyanine or polybromochloro-copper phthalocyanine containing up to 14 bromine atoms per molecule and mixtures thereof. In another aspect, suitable pigments include pigments selected from the group consisting of Ultramarine Blue (C.I. Pigment Blue 29), Ultramarine Violet (C.I. Pigment Violet 15), Monastral Blue and mixtures thereof.

In one aspect, materials suitable for incorporation into the benefit agent containing delivery particles of the present invention include leuco dyes, antioxidants, and mixtures thereof. Leuco dyes are known in the prior art to exhibit a change from a colorless or slightly colored state to a colored state upon exposure to specific chemical or physical triggers. The chemical or physical triggers that bring about the coloration change include, but are not limited to, oxidation, intramolecular ring opening, pH change, and exposure to heat and/or cold or light (e.g. UV light). Preferred Leuco dyes include those that develop a color upon triggering that is suitable for use as a shading dye to increase whiteness perception. Triarylmethane compounds are a class of leuco dyes useful in one aspect.

The aforementioned fabric hueing agents can be used in combination (any mixture of fabric hueing agents can be used).

Water

The graft co-polymer and benefit agent can be optionally further combined with water to form feedstock compositions that can be later combined with consumer product adjunct ingredients to form consumer product compositions. The graft co-polymer and benefit agent can be optionally further combined with water and consumer product adjunct ingredients as part of the same process to form consumer product compositions.

Water is utilized in the present processes and resulting compositions (including feedstock compositions and/or consumer product compositions) at levels of less than about 98%, preferably less than about 96%, preferably less than about 90% by weight of the composition, of water. Water can be utilized at levels of from about 1% to about 98%, preferably from about 5% to about 95%, preferably from about 5% to about 90%, preferably from about 5% to about 85%, preferably from about 5% to about 70%, by weight of the composition, of water.

Benefit Agent Delivery Particles

The processes of the present invention wherein the graft co-polymer and benefit agent are premixed, leads to the formation of benefit agent delivery particles in the resulting compositions. It is believed that the graft co-polymer and benefit agent self-assemble into such benefit agent delivery particles when premixed and added to water and/or consumer product adjunct ingredients to form compositions comprising the benefit agent delivery particles.

The size of the benefit agent delivery particles in the compositions can have at least one particle having and/or a number-weighted average diameter of the benefit agent delivery particles of:

a) a diameter of from about 0.5 microns to about 5000 microns, preferably from about 0.5 microns to about 1000 microns, more preferably from about 0.5 microns to about 250 microns, most preferably from about 1 microns to about 60 microns;

b) a diameter of from about 0.01 microns to about 0.5 microns, preferably from about 0.02 microns to about 0.5 microns, more preferably from about 0.04 microns to about 0.5 microns; or c) a diameter of from about 250 microns to about 10,000 microns, preferably from about 250 microns to about 7500 microns, more preferably from about 500 microns to about 5000 microns, most preferably from about 750 microns to about 2500 microns;
depending on the desired size of particles in the compositions of the present invention. The particle size is determined according to the Particle Diameter and Structure Test Method hereinbelow.

The benefit agent delivery particles can have an intensity-averaged hydrodynamic diameter of from about 10 to about 100 nanometers, more preferably from about 15 to about 80 nanometers, and more preferably from about 20 to about 60 nanometers, as determined by the Hydrodynamic Diameter of Particles Test Method hereinbelow.

The benefit agent delivery particles preferably have a weight ratio of benefit agent to graft co-polymer of from 1:20 to 20:1, preferably from 4:1 to 20:1. The weight ratio is the ratio between the total weight of the benefit agents and the total weight of the graft co-polymers of the benefit agent delivery particles.

The benefit agent delivery particles can have a structure selected from the group consisting of:

a) a benefit agent delivery particle comprising a single region of benefit agent that is embedded in the graft co-polymer;

b) a benefit agent delivery particle comprising at least two regions of benefit agent that are embedded in the graft co-polymer;

c) a benefit agent delivery particle comprising at least one region of benefit agent that are at least partially embedded on the surface of the graft co-polymer;

d) a benefit agent delivery particle comprising a single region of benefit agent that is embedded in the graft co-polymer and at least one region of benefit agent that is at least partially embedded on the surface of the graft co-polymer; and e) a benefit agent delivery particle comprising at least two regions of benefit agent that are embedded in the graft co-polymer and at least one region of benefit agent that is at least partially embedded on the surface of the graft co-polymer.

Water Binding Agents

A water binding agent can optionally be added to a liquid composition to lower its free water content. The water binding agents comprise organic acids, salts of organic acids, humectants, desiccants, natural sugar substitutes, artificial sugar substitutes, hydrogels and/or mixtures thereof.

Organic acids and salts thereof can be selected but not limited from the group consisting of citric acid, maleic acid, fumaric acid, salts thereof or mixtures thereof, preferably citric acid or salts thereof.

Humectants can be selected but not limited from the group consisting of 1,2,6-hexanetriol, butylene glycol, dipropylene glycol, glycerin, hexylene, glycol, panthenol, phytantriol, propylene glycol, sorbitol, triethylene glycol, polyglyceryl sorbitol, glucose, fructose, polydextrose, urea, hyaluronic acid, inositol, hexanediol beeswax, hexanetriol beeswax, hydrolyzed elastin, hydrolyzed collagen, hydrolyzed silk, hydrolyzed keratin, erythritol, capryl glycol, isoceteth-(3-10, 20, 30), isolaureth-(3-10, 20, 30), laneth-(5-50), laureth-(1-30), steareth-(4-20), trideceth-(5-50).

Desiccants can be selected but not limited from the group consisting of activated alumina, aerogel, benzophenone, bentonite clay, calcium chloride, calcium sulfate, cobalt(ii) chloride, copper(ii) sulfate, lithium chloride, lithium bromide, magnesium sulfate, magnesium perchlorate, molecular sieve, potassium carbonate, silica gel, sodium chlorate, sodium chloride, sodium hydroxide, sodium sulfate, sucrose.

Natural sugar substitutes can be selected but not limited from the group consisting of brazzein, curculin, erythritol, glycyrrhizin, glycerol, hydrogenated starch hydrolysates, inulin, isomalt, lactitol, luo han guo, mabinlin, maltitol, mannitol, miraculin, monatin, sclemchiton ilicifolius, monellin berries, osladin, pentadin, sorbitol, stevia, tagatose, thaumatin, xylitol.

Artificial sugar substitutes can be selected but not limited from the group consisting of aspartame, salts of aspartame, cyclamate, dulcin, glucin, neohesperidin dihydrochalcone, saccharin, sucralose.

Hydrogels can be selected but not limited from the group consisting of hydrogel forming polymers like silicone hydrogels, polyacrylamides, cross-linked polymers, polyethylene oxide, polyvinylpyrrolidone, polyvinyl alcohol, sodium polyacrylate, acrylate, or agarose, methylcellulose, hyaluronan, and other naturally derived polymers.

Consumer Product Adjunct Materials

The disclosed consumer product compositions may include additional consumer product adjunct materials (otherwise referenced herein as adjunct materials) that are in addition to the materials found in the benefit agent delivery particles. Such adjunct materials are typically added to the consumer product compositions separate from the graft co-polymer and benefit agents which form the benefit agent delivery particles herein. Such adjunct ingredients may include: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, fabric softeners, carriers, hydrotropes, processing aids, structurants, anti-agglomeration agents, coatings, scavengers and/or pigments. Other embodiments of Applicants' compositions do not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, fabric softeners, carriers, hydrotropes, processing aids, structurants, anti-agglomeration agents, coatings, formaldehyde scavengers and/or pigments. The precise nature of these additional components, and levels of incorporation thereof, will depend on the physical form of the composition and the nature of the operation for which it is to be used. However, when one or more adjuncts are present, such one or more adjuncts may be present as detailed below. Preferred consumer product adjunct materials herein are selected from the group consisting of surfactants, builders, dispersants, enzymes, dye transfer inhibiting agents, chelants, brighteners, bleach systems and bleaching agents, stabilizers, silicones, perfumes, fabric hueing agents, anti-agglomeration agents, and mixtures thereof. The following is a non-limiting list of suitable additional adjuncts.

Surfactants—Surfactants utilized can be of the anionic, nonionic, zwitterionic, ampholytic or cationic type or can comprise compatible mixtures of these types. Anionic and nonionic surfactants are typically employed if the consumer product composition is a laundry detergent or hair shampoo. On the other hand, cationic surfactants are typically employed if the consumer product composition is a fabric softener or hair conditioner. In addition to the anionic surfactant, the consumer product compositions of the present invention may further contain a nonionic surfactant. The compositions of the present invention can contain up to about 30%, alternatively from about 0.01% to about 20%, more alternatively from about 0.1% to about 10%, by weight of the composition, of a nonionic surfactant. In one embodiment, the nonionic surfactant may comprise an ethoxylated nonionic surfactant. Suitable for use herein are the ethoxylated alcohols and ethoxylated alkyl phenols of the formula $R(OC_2H_4)n$ OH, wherein R is selected from the group consisting of aliphatic hydrocarbon radicals containing from about 8 to about 20 carbon atoms and alkyl phenyl radicals in which the alkyl groups contain from about 8 to about 12 carbon atoms, and the average value of n is from about 5 to about 15.

Suitable nonionic surfactants are those of the formula $R1(OC_2H_4)nOH$, wherein R1 is a $C_{10}$-$C_{16}$ alkyl group or a $C_8$-$C_{12}$ alkyl phenyl group, and n is from 3 to about 80. In one aspect, particularly useful materials are condensation products of $C_9$-$C_{15}$ alcohols with from about 5 to about 20 moles of ethylene oxide per mole of alcohol.

The consumer product compositions of the present invention may contain up to about 30%, alternatively from about 0.01% to about 20%, more alternatively from about 0.1% to about 20%, by weight of the composition, of a cationic surfactant. For the purposes of the present invention, cationic surfactants include those which can deliver fabric softening or hair conditioning benefits. Non-limiting examples of useful cationic surfactants include: fatty amines, imidazoline quat materials and quaternary ammonium surfactants, preferably N, N-bis(stearoyl-oxy-ethyl) N,N-dimethyl ammonium chloride, N,N-bis(tallowoyl-oxy-ethyl) N,N-dimethyl ammonium chloride, N,N-bis(stearoyl-oxy-ethyl)N-(2 hydroxyethyl)N-methyl ammonium methylsulfate; 1, 2 di (stearoyl-oxy) 3 trimethyl ammoniumpropane chloride; dialkylenedimethylammonium salts such as dicanoladimethylammonium chloride, di(hard)tallowdimethylammonium chloride dicanoladimethylammonium methylsulfate; 1-methyl-1-stearoylamidoethyl-2-stearoylimidazolinium methylsulfate; 1-tallowylamidoethyl-2-tallowylimidazoline; N,N"-dialkyldiethylenetriamine; the reaction product of N-(2-hydroxyethyl)-1,2-ethylenediamine or N-(2-hydroxyisopropyl)-1,2-ethylenediamine with glycolic acid, esterified with fatty acid, where the fatty acid is (hydrogenated) tallow fatty acid, palm fatty acid, hydrogenated palm fatty acid, oleic acid, rapeseed fatty acid, hydrogenated rapeseed fatty acid; polyglycerol esters (PGEs), oily sugar derivatives, and wax emulsions and a mixture of the above.

Builders—The compositions may also contain from about 0.1% to 80% by weight of a builder. Compositions in liquid form generally contain from about 1% to 10% by weight of the builder component. Compositions in granular form generally contain from about 1% to 50% by weight of the builder component. Detergent builders are well known in the art and can contain, for example, phosphate salts as well as various organic and inorganic nonphosphorus builders. Water-soluble, nonphosphorus organic builders useful herein include the various alkali metal, ammonium and substituted ammonium polyacetates, carboxylates, polycarboxylates and polyhydroxy sulfonates. Examples of polyacetate and polycarboxylate builders are the sodium, potassium, lithium, ammonium and substituted ammonium salts of ethylene diamine tetraacetic acid, nitrilotriacetic acid, oxydisuccinic acid, mellitic acid, benzene polycarboxylic acids, and citric acid. Other polycarboxylate builders are the oxydisuccinates and the ether carboxylate builder compositions comprising a combination of tartrate monosuccinate and tartrate disuccinate. Builders for use in liquid detergents include citric acid. Suitable nonphosphorus, inorganic builders include the silicates, aluminosilicates, borates and carbonates, such as sodium and potassium carbonate, bicarbonate, sesquicarbonate, tetraborate decahydrate, and silicates having a weight ratio of $SiO2$ to alkali metal oxide of from about 0.5 to about 4.0, or from about 1.0 to about 2.4. Also useful are aluminosilicates including zeolites.

Dispersants—The compositions may contain from about 0.1%, to about 10%, by weight of dispersants. Suitable dispersants are water-soluble organic materials are the homo- or co-polymeric acids or their salts, in which the polycarboxylic acid may contain at least two carboxyl radicals separated from each other by not more than two carbon atoms. The dispersants may also be alkoxylated derivatives of polyamines, and/or quaternized derivatives.

Enzymes—The compositions may contain one or more detergent enzymes which provide cleaning performance and/or fabric care benefits. Examples of suitable enzymes include hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, DNases and amylases, or mixtures thereof. A typical combination may be a cocktail of conventional applicable enzymes like protease, lipase, cutinase and/or cellulase in conjunction with amylase. Enzymes can be used at their art-taught levels, for example at levels recommended by suppliers such as Novozymes and Genencor. Typical levels in the compositions are from about 0.0001% to about 5%. When enzymes are present, they can be used at very low levels, e.g., from about 0.001% or lower, or they can be used in heavier-duty laundry detergent formulations at higher levels, e.g., about 0.1% and higher. In accordance with a preference of some consumers for "non-biological" detergents, the compositions may be either or both enzyme-containing and enzyme-free.

Dye Transfer Inhibiting Agents—The compositions may also include from about 0.0001%, from about 0.01%, from about 0.05% by weight of the compositions to about 10%, about 2%, or even about 1% by weight of the compositions of one or more dye transfer inhibiting agents such as polyvinylpyrrolidone polymers, polyamine N-oxide polymers, copolymers of N-vinylpyrrolidone and N-vinylimidazole, polyvinyloxazolidones and polyvinylimidazoles or mixtures thereof.

Chelant—The compositions may contain less than about 5%, or from about 0.01% to about 3% of a chelant such as citrates; nitrogen-containing, P-free aminocarboxylates such as EDDS, EDTA and DTPA; aminophosphonates such as diethylenetriamine pentamethylenephosphonic acid and, ethylenediamine tetramethylenephosphonic acid; nitrogen-free phosphonates e.g., HEDP; and nitrogen or oxygen containing, P-free carboxylate-free chelants such as compounds of the general class of certain macrocyclic N-ligands such as those known for use in bleach catalyst systems.

Brighteners—The compositions may also comprise a brightener (also referred to as "optical brightener") and may include any compound that exhibits fluorescence, including compounds that absorb UV light and reemit as "blue" visible light. Non-limiting examples of useful brighteners include: derivatives of stilbene or 4,4'-diaminostilbene, biphenyl, five-membered heterocycles such as triazoles, pyrazolines, oxazoles, imidiazoles, etc., or six-membered heterocycles (coumarins, naphthalamide, s-triazine, etc.). Cationic, anionic, nonionic, amphoteric and zwitterionic brighteners can be used. Suitable brighteners include those commercially marketed under the trade name Tinopal-UNPA-GX® by Ciba Specialty Chemicals Corporation (High Point, N.C.).

Bleach system—Bleach systems suitable for use herein contain one or more bleaching agents. Non-limiting examples of suitable bleaching agents include catalytic metal complexes; activated peroxygen sources; bleach activators; bleach boosters; photobleaches; bleaching enzymes; free radical initiators; $H_2O_2$; hypohalite bleaches; peroxygen sources, including perborate and/or percarbonate and combinations thereof. Suitable bleach activators include perhydrolyzable esters and perhydrolyzable imides such as, tetraacetyl ethylene diamine, octanoylcaprolactam, benzoyloxybenzenesulphonate, nonanoyloxybenzene¬ sulphonate, benzoylvalerolactam, dodecanoyloxybenzenesulphonate. Other bleaching agents include metal complexes of transitional metals with ligands of defined stability constants.

Stabilizer—The compositions may contain one or more stabilizers and thickeners. Any suitable level of stabilizer may be of use; exemplary levels include from about 0.01% to about 20%, from about 0.1% to about 10%, or from about 0.1% to about 3% by weight of the composition. Non-limiting examples of stabilizers suitable for use herein include crystalline, hydroxyl-containing stabilizing agents, trihydroxystearin, hydrogenated oil, or a variation thereof, and combinations thereof. In some aspects, the crystalline, hydroxyl-containing stabilizing agents may be water-insoluble wax-like substances, including fatty acid, fatty ester or fatty soap. In other aspects, the crystalline, hydroxyl-containing stabilizing agents may be derivatives of castor oil, such as hydrogenated castor oil derivatives, for example, castor wax. Other stabilizers include thickening stabilizers such as gums and other similar polysaccharides, for example gellan gum, carrageenan gum, and other known types of thickeners and rheological additives. Exemplary stabilizers in this class include gum-type polymers (e.g. xanthan gum), polyvinyl alcohol and derivatives thereof, cellulose and derivatives thereof including cellulose ethers and cellulose esters and tamarind gum (for example, comprising xyloglucan polymers), guar gum, locust bean gum (in some aspects comprising galactomannan polymers), and other industrial gums and polymers.

Other examples of suitable stabilizers may include hydrogenated and non-hydrogenated polyalkenes, and mixtures thereof; inorganic salts, for example, magnesium chloride, calcium chloride, calcium formate, magnesium formate, aluminum chloride, potassium permanganate, laponite clay, bentonite clay and mixtures thereof; polysaccharides in combination with inorganic salts; quaternized polymeric materials, for example, polyether amines, alkyl trimethyl ammonium chlorides, diester ditallow ammonium chloride; imidazoles; nonionic polymers with a pKa less than 6.0, for example polyethyleneimine, polyethyleneimine ethoxylate; polyurethanes. Such materials can be obtained from CP Kelco Corp. of San Diego, Calif., USA; Degussa AG or Dusseldorf, Germany; BASF AG of Ludwigshafen, Germany; Rhodia Corp. of Cranbury, N.J., USA; Baker Hughes Corp. of Houston, Tex., USA; Hercules Corp. of Wilmington, Del., USA; Agrium Inc. of Calgary, Alberta, Canada, ISP of New Jersey, U.S.A.

Silicones—Suitable silicones comprise Si—O moieties and may be selected from (a) non-functionalized siloxane polymers, (b) functionalized siloxane polymers, and combinations thereof. The molecular weight of the organosilicone is usually indicated by the reference to the viscosity of the material. In one aspect, the organosilicones may comprise a viscosity of from about 10 to about 2,000,000 centistokes at 25° C. In another aspect, suitable organosilicones may have a viscosity of from about 10 to about 800,000 centistokes at 25° C.

Suitable organosilicones may be linear, branched or cross-linked.

In one aspect, the organosilicone may comprise a cyclic silicone. The cyclic silicone may comprise a cyclomethicone of the formula $[(CH_3)_2SiO]n$ where n is an integer that may range from about 3 to about 7, or from about 5 to about 6.

In one aspect, the organosilicone may comprise a functionalized siloxane polymer. Functionalized siloxane polymers may comprise one or more functional moieties selected from the group consisting of amino, amido, alkoxy, hydroxy, polyether, carboxy, hydride, mercapto, sulfate phosphate, and/or quaternary ammonium moieties. These moieties may be attached directly to the siloxane backbone through a bivalent alkylene radical, (i.e., "pendant") or may be part of the backbone. Suitable functionalized siloxane polymers include materials selected from the group consisting of aminosilicones, amidosilicones, silicone polyethers, silicone-urethane polymers, quaternary ABn silicones, amino ABn silicones, and combinations thereof.

In one aspect, the functionalized siloxane polymer may comprise a silicone polyether, also referred to as "dimethicone copolyol." In general, silicone polyethers comprise a polydimethylsiloxane backbone with one or more polyoxyalkylene chains. The polyoxyalkylene moieties may be incorporated in the polymer as pendent chains or as terminal blocks. In another aspect, the functionalized siloxane polymer may comprise an aminosilicone.

In one aspect, the organosilicone may comprise amine ABn silicones and quat ABn silicones. Such organosilicones are generally produced by reacting a diamine with an epoxide.

In another aspect, the functionalized siloxane polymer may comprise silicone-urethanes. These are commercially available from Wacker Silicones under the trade name SLM-21200®.

Perfume—The perfume component may comprise a component selected from the group consisting of:

(1) a neat perfume oil;

(2) a perfume capsule, or a moisture-activated perfume capsule, comprising a perfume carrier and an encapsulated perfume composition, wherein said perfume carrier may be selected from the group consisting of cyclodextrins, starch capsules, porous carrier capsules, and mixtures thereof; and wherein said encapsulated perfume composition may comprise low volatile perfume ingredients, high volatile perfume ingredients, and mixtures thereof;

(3) a pro-perfume;

(4) a low odor detection threshold perfume ingredients, wherein said low odor detection threshold perfume ingredients may comprise less than about 25%, by weight of the total neat perfume composition; and (6) mixtures thereof.

Such perfumes as a consumer product adjunct material are incorporated into the consumer product composition separate from the benefit agent delivery particles and are typically present in a phase separate from the benefit agent delivery particles in the consumer product composition.

Fabric Hueing Agents—The composition may comprise a fabric hueing agent (sometimes referred to as shading, bluing or whitening agents). Typically the hueing agent provides a blue or violet shade to fabric. Hueing agents can be used either alone or in combination to create a specific shade of hueing and/or to shade different fabric types. This may be provided for example by mixing a red and green-blue dye to yield a blue or violet shade. Hueing agents may be selected from any known chemical class of dye, including but not limited to acridine, anthraquinone (including polycyclic quinones), azine, azo (e.g., monoazo, disazo, trisazo, tetrakisazo, polyazo), including premetallized azo, benzodifurane and benzodifuranone, carotenoid, coumarin, cyanine, diazahemicyanine, diphenylmethane, formazan, hemicyanine, indigoids, methane, naphthalimides, naphthoquinone, nitro and nitroso, oxazine, phthalocyanine, pyrazoles, stilbene, styryl, triarylmethane, triphenylmethane, xanthenes and mixtures thereof.

Suitable fabric hueing agents include dyes, dye-clay conjugates, and organic and inorganic pigments. Suitable dyes include small molecule dyes and polymeric dyes. Suitable small molecule dyes include small molecule dyes selected from the group consisting of dyes falling into the Colour Index (C.I.) classifications of Acid, Direct, Basic, Reactive (or hydrolysed forms thereof), Solvent or Disperse dyes for example that are classified as Blue, Violet, Red, Green or Black, and provide the desired shade either alone or in combination. In another aspect, suitable small molecule dyes include small molecule dyes selected from the group consisting of Colour Index (Society of Dyers and Colourists, Bradford, UK) numbers Direct Violet dyes such as 9, 35, 48, 51, 66, and 99, Direct Blue dyes such as 1, 71, 80 and 279, Acid Red dyes such as 17, 73, 52, 88 and 150, Acid Violet dyes such as 15, 17, 24, 43, 49 and 50, Acid Blue dyes such as 15, 17, 25, 29, 40, 45, 75, 80, 83, 90 and 113, Acid Black dyes such as 1, Basic Violet dyes such as 1, 3, 4, 10 and 35, Basic Blue dyes such as 3, 16, 22, 47, 66, 75 and 159, Disperse or Solvent dyes as disclosed in U.S. Pat. No. 8,268,016 B2, or dyes as disclosed in U.S. Pat. No. 7,208,459 B2, or dyes disclosed in U.S. Pat. No. 8,247,364 B2 and mixtures thereof. In another aspect, suitable small molecule dyes include small molecule dyes selected from the group consisting of C. I. numbers Acid Violet 17, Acid Blue 80, Acid Violet 50, Direct Blue 71, Direct Violet 51, Direct Blue 1, Acid Red 88, Acid Red 150, Acid Blue 29, Acid Blue 113, fabric hueing agents that undergo a transition on storage or during or after use that either (1) changes the extinction coefficient in the visible range at a set wavelength (400-750 nm) from less than 1000 $M^{-1}$ $cm^{-1}$ to one greater than 5,000, preferably greater than 10,000, more preferably greater than 20,000, even more preferably greater than 50,000, most preferably greater than 80,000 or even 100,000 $M^{-1}$ $cm^{-1}$, (2) increases the extinction coefficient in the visible range at a set wavelength (400-750 nm) by a factor of at least five, preferably ten or even twenty fold wherein the final extinction coefficient at the set wavelength is at least 10,000 $M^{-1}$ $cm^{-1}$, or (3) shifts the wavelength of the maximum extinction coefficient within the visible range from the pre-transition value by at least 25 nm, preferably 50 nm, even more preferably 75 nm, most preferably by 100 nm or more, wherein the final wavelength of the maximum extinction coefficient within the visible range is from about 550 to 700 nm, preferably from 550 to 650 nm, and/or mixtures thereof.

Suitable polymeric dyes include polymeric dyes selected from the group consisting of polymers containing covalently bound (sometimes referred to as conjugated) chromogens, (dye-polymer conjugates), for example polymers with chromogens co-polymerized into the backbone of the polymer and mixtures thereof. Polymeric dyes include those described in U.S. Pat. No. 7,686,892 B2.

In another aspect, suitable polymeric dyes include polymeric dyes selected from the group consisting of fabric-substantive colorants sold under the name of Liquitint® (Milliken, Spartanburg, S.C., USA), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. In still another aspect, suitable polymeric dyes include polymeric dyes selected from the group consisting of Liquitint® Violet CT, carboxymethyl cellulose (CMC) covalently bound to a reactive blue, reactive violet or reactive red dye such as CMC conjugated with C.I. Reactive Blue 19, sold by Megazyme, Wicklow, Ireland under the product name AZO-CM-CELLULOSE, product code S-ACMC, alkoxylated triphenylmethane polymeric colourants, alkoxylated thiophene polymeric colourants, and mixtures thereof.

Suitable dye clay conjugates include dye clay conjugates selected from the group comprising at least one cationic/basic dye and a smectite clay, and mixtures thereof. In another aspect, suitable dye clay conjugates include dye clay conjugates selected from the group consisting of one cationic/basic dye selected from the group consisting of C.I. Basic Yellow 1 through 108, C.I. Basic Orange 1 through 69, C.I. Basic Red 1 through 118, C.I. Basic Violet 1 through 51, C.I. Basic Blue 1 through 164, C.I. Basic Green 1 through 14, C.I. Basic Brown 1 through 23, CI Basic Black 1 through 11, and a clay selected from the group consisting of Montmorillonite clay, Hectorite clay, Saponite clay and mixtures thereof. In still another aspect, suitable dye clay conjugates include dye clay conjugates selected from the group consisting of: Montmorillonite Basic Blue B7 C.I. 42595 conjugate, Montmorillonite Basic Blue B9 C.I. 52015 conjugate, Montmorillonite Basic Violet V3 C.I. 42555 conjugate, Montmorillonite Basic Green G1 C.I. 42040 conjugate, Montmorillonite Basic Red R1 C.I. 45160 conjugate, Montmorillonite C.I. Basic Black 2 conjugate, Hectorite Basic Blue B7 C.I. 42595 conjugate, Hectorite Basic Blue B9 C.I. 52015 conjugate, Hectorite Basic Violet V3 C.I. 42555 conjugate, Hectorite Basic Green G1 C.I. 42040 conjugate, Hectorite Basic Red R1 C.I. 45160 conjugate, Hectorite C.I. Basic Black 2 conjugate, Saponite Basic Blue B7 C.I. 42595 conjugate, Saponite Basic Blue B9 C.I. 52015 conjugate, Saponite Basic Violet V3 C.I. 42555 conjugate, Saponite Basic Green G1 C.I. 42040 conjugate, Saponite Basic Red R1 C.I. 45160 conjugate, Saponite C.I. Basic Black 2 conjugate and mixtures thereof.

The hueing agent may be incorporated into the detergent composition as part of a reaction mixture which is the result of the organic synthesis for a dye molecule, with optional purification step(s). Such reaction mixtures generally comprise the dye molecule itself and in addition may comprise un-reacted starting materials and/or by-products of the organic synthesis route.

Suitable polymeric bluing agents may be alkoxylated. As with all such alkoxylated compounds, the organic synthesis may produce a mixture of molecules having different degrees of alkoxylation. Such mixtures may be used directly to provide the hueing agent, or may undergo a purification step to increase the proportion of the target molecule.

Suitable pigments include pigments selected from the group consisting of flavanthrone, indanthrone, chlorinated indanthrone containing from 1 to 4 chlorine atoms, pyranthrone, dichloropyranthrone, monobromodichloropyranthrone, dibromodichloropyranthrone, tetrabromopyranthrone, perylene-3,4,9,10-tetracarboxylic acid diimide, wherein the imide groups may be unsubstituted or substituted by $C_1$-$C_3$-alkyl or a phenyl or heterocyclic radical, and wherein the phenyl and heterocyclic radicals may additionally carry substituents which do not confer solubility in water, anthrapyrimidinecarboxylic acid amides, violanthrone, isoviolanthrone, dioxazine pigments, copper phthalocyanine which may contain up to 2 chlorine atoms per molecule, polychloro-copper phthalocyanine or polybromochloro-copper phthalocyanine containing up to 14 bromine atoms per molecule and mixtures thereof. In another aspect, suitable pigments include pigments selected from the group consisting of Ultramarine Blue (C.I. Pigment Blue 29), Ultramarine Violet (C.I. Pigment Violet 15), Monastral Blue and mixtures thereof.

The aforementioned fabric hueing agents can be used in combination (any mixture of fabric hueing agents can be used).

Anti-agglomeration agents—Useful anti-agglomeration agent materials include, divalent salts such as magnesium salts, for example, magnesium chloride, magnesium acetate, magnesium phosphate, magnesium formate, magnesium boride, magnesium titanate, magnesium sulfate heptahydrate; calcium salts, for example, calcium chloride, calcium formate, calcium acetate, calcium bromide; trivalent salts, such as aluminum salts, for example, aluminum sulfate, aluminum phosphate, aluminum chloride hydrate and polymers that have the ability to suspend anionic particles such as suspension polymers, for example, polyethylene imines, alkoxylated polyethylene imines, polyquaternium-6 and polyquaternium-7.

Compositions Obtainable by the Process

The present invention further relates to compositions obtainable by the processes of the present invention. Such compositions include feedstock compositions and consumer product compositions, each of which comprise benefit agent delivery particles that comprise graft co-polymer and benefit agent. The compositions of the present invention are preferably liquid compositions.

Feedstock compositions are obtainable by premixing the graft co-polymer and benefit agent, in further combination with water to form the feedstock compositions. Such feedstock compositions will comprise less than about 98%, preferably less than about 96%, preferably less than about 90% by weight of the feedstock composition, of water. Water can be utilized at levels of from about 1% to about 98%, preferably from about 5% to about 95%, preferably from about 5% to about 90%, preferably from about 5% to about 85%, preferably from about 5% to about 70%, by weight of the feedstock composition, of water. Such feedstock compositions will preferably have a Free Water Content (as measured by the Free Water Content Test Method) of less than about 96%, preferably less than about 90%, and preferably from about 5% to about 90%. Such feedstock compositions can be produced, stored, and shipped to another manufacturing location to be further combined with consumer product adjunct material(s) to form consumer product compositions.

Consumer product compositions are also obtainable by premixing the graft co-polymer and benefit agent to form a premix composition, and further combining the premix composition with consumer product adjunct material(s) to form a consumer product composition of the present invention. Such consumer product compositions will preferably comprise water at a level of less than about 98%, preferably less than about 96%, preferably less than about 90% by weight of the consumer product composition. Water can be utilized at levels of from about 1% to about 98%, preferably from about 5% to about 95%, preferably from about 5% to about 90%, preferably from about 5% to about 85%, preferably from about 5% to about 70%, by weight of the consumer product composition, of water.

The finished consumer product compositions of the present invention can comprise a certain Free Water Content, as determined by the Free Water Content Test Method described hereinbelow. Preferably, the compositions of the present invention comprise a Free Water Content of less than about 96%, preferably less than about 90%, and preferably from about 5% to about 90%. When the consumer product composition is:
(i) a unit dose composition, the Free Water Content is preferably from about 5% to about 10%;
(ii) a liquid detergent, the Free Water Content is preferably from about 10% to about 70%;
(iii) a liquid fabric enhancer, the Free Water Content is preferably from about 80% to about 95%;
(iv) a surface care cleaning composition, the Free Water Content is preferably from about 85% to about 96%;
(v) a skin care composition, the Free Water Content is preferably from about 20% to about 96%; and
(vi) a hair cleaning and/or conditioning composition, the Free Water Content is preferably from about 20% to about 96%.

Test Methods

It is understood that the test methods that are disclosed in the Test Methods Section of the present application should be used to determine the respective values of the parameters of Applicants' invention as such invention is described and claimed herein.

Hydrodynamic Diameter of Particles Test Method

This method is used to determine the intensity-averaged hydrodynamic diameter of particles via Dynamic Light Scattering (DLS). The DLS apparatus comprises a model 9000 AT correlator and a model 200 SM goniometer, plus accompanying Dynamic Light Scattering Software (vers. 5.78) (all from Brookhaven Instruments, USA), or equivalents. The system is equipped with temperature thermostat, and an EMI 9863B/350 photomultiplier, or equivalent and a Coherent DPY315M-100 Nd:YAG laser ($\lambda$=532 nm) which is linearly polarized in the vertical direction. The thermostat is set to 25° C. Click on "Control", then "Motor", then "Set Angle" and select 900. Set the Pinhole to 100 and open the correlator shutter to the laser position (532). Place 1.5 ml of sample into a test tube (such as 12×75 mm Disposable Borosilicate Glass Test Tube) and centrifuge the tube and sample at 4000 rpm for 5 minutes. Put the test containing the test sample into the DLS instrument. In the Software click on "Correlation Functions", then "New Window", and then click "OK". A "Correlator Control Window" appears, press on Start (green button) and check the Average Count Rate (A CR). If A CR>500 kcps stop the measurement and dilute the sample and repeat until an A CR value less than 500 kcps is obtained. Click on "Graphs", then "Correlation Functions", and then "New Window". Click on "ISDA", then on "Cumulant Analysis", and then on "New Window". In the "Correlator Control Window" click on "Params" and add the sample parameters; including: select water as Liquid; select 90 at Angle' enter 532 at Wavelength; Flag "Use dust filter". In the "Correlator Control Window" click on "Dur", then on "Elapsed time" and select 2 minutes. In the "Correlator Control Window" click on "Layout" and optimize the first and last delay depending on the autocorrelation curve. In the "Correlator Control Window" press Start and wait until the measurement is completed. The intensity-averaged Hydrodynamic Diameter value is reported in the "Cumulant Analysis" window, and is reported in units of nanometers.

Particle Diameter and Structure Test Method

Microscopy is used to measure the number-weighted average diameter of the co-polymer particles. Microscopy is also used to determine the structure of the particles via observing the frequency and the location of benefit agent regions in the particles. The microscopic measurement particle diameter may be conducted using any microscopic technique capable of imaging the external size of the particles in the sample. The microscopic determination of structure may be conducted using any microscopic technique capable of imaging the internal presence and location of the benefit agent regions in the particles. Suitable microscopy techniques may include but are not limited to: Scanning Electron Microscopy (SEM); Phase Contrast Microscopy; Differential Interference Contrast microsopy (DIC); Fluorescence Microscopy; and Confocal Laser Scanning Fluorescence Microscopy (CLSM). One of skill will understand that different and various sample preparation steps may be required for the different imaging techniques which may be suitable. In all cases, the number-weighted average diameter of the particles is calculated from the values obtained by microscopically observing and measuring the diameter of at least 30 randomly selected particles in a sample.

The structure of the particles is assessed by microscopically observing and determining the frequencies and locations of all observable benefit agent regions in at least 30 randomly selected particles in a sample. In the case of optical light microscopy techniques it is suitable to use a high magnification water-immersion objective lens such as a 63×/1.2 NA Water lens (Zeiss) to observe 0.5 mL of sample placed into a Chambered Coverglass such as Chambered #1.0 Borosilicate Coverglass System (such as from LabTek) and to dilute the sample as necessary to obtain unobstructed images of the particle diameter and structure. In the case of fluorescence microscopy and especially fluorescence confocal laser scanning microsopy (CLSM), the selective labeling of the polymers and the benefit agents with different fluorescent dyes can enable their separate detection via excitation with different wavelengths of light. For example, by labeling the polymer(s) with a red dye label such as Rhodamine isothiocyanate (λex=561 nm), and the benefit agents with a dye probe having a different excitation wavelength, for example such as Coumarin 6 (λex=488 nm), it is then possible to determine where the polymer and the benefit agents are located by means of different filters and detectors on the microscope. By using the overlay of images from the different detectors it is possible to identify the regions of co-localization, and observe the frequency and spatial location of the benefit agent regions relative to the particle and its polymer regions.

In the examples, an amphiphilic polymer has been labeled with Rhodamine isothiocyanate λex=561 nm and imaged via Confocal Laser Scanning Fluorescence Microscopy. This method permits easy observation and determination of the structure of the particles.

Free Water Content Test Method

Free water content (FWC) refers to the amount of freezable non-bound water with a temperature of fusion around 0° C. and is defined as:

$$FWC\% = \left(\frac{\Delta H_{f,sample} * m_{sample}}{\Delta H_{f,H_2O}}\right) / m_{sample} * 100$$

where $\Delta H_{f,sample}$ is the enthalpy of fusion of water in the sample in J/g, mm is the weight of the sample in g, and $\Delta H_{f,H2O}$ is the enthalpy of fusion of pure water in J/g.

Materials

Differential scanning calorimetry with refrigerated cooling system, such as DSC-Q2000 with DSC software Advantage for Q series version 5.4.0, and Analysis software such as Universal analysis 2000 version 4.5A (TA instruments), or equivalents.

Analytical balance (sensitivity 0.0001 g), such as Sartorius CP225D.

DSC Steel pan, such as Perkin Elmer model: 0319-1525 (bottom) 0319-1526 (cover) 0319-1535 (O-ring)

Procedure to measure $\Delta H_{f,sample}$

1) Weight on the balance the Steel pan with its cover and the O-ring. Note the weight ($W_p$)
2) Assemble the O-ring with the cover
3) Weight on the balance the amount of sample (10-20 mg) added into the pan, note the weight ($W_{s+p}$)
4) Close the pan hermetically
5) Calculate $W_s = W_{s+p} - W_p$
6) Insert the pan in the DSC
7) Open the Nitrogen line (flow must be not below 50 ml/min)
8) Open the software TA instrument explorer
9) Turn on the cooler from the button control and then press "event on" on the software
10) The software is subdivided into three main parts. (Summary-procedure-notes). In summary you have to write the details of the sample (sample name, $W_p$, $W_s$) and the type of pan you are using, then select the directory to save the data and flag "pan mass". In the 'Procedure' panel by pressing 'Editor' you can write down the procedure needed for your samples. Here we report the procedure used to calculate the FWC.

Equilibrate at 5° C.
Data storage on
Ramp 0.5°/min to −80° C.
Mark the end of the cycle "O"
Ramp 0.5° C./min to 25° C.
Mark the end of the cycle "1"

In the 'notes' panel choose the appropriate calibration in this case (Steel pan 0.5° C./min)

11) Press 'apply' button to complete the run procedure and start from the main software panel.
12) Once the run is done it will be green flagged Procedure to analyze the data
1) Open the data collected with the DSC, using the analysis software (Universal analysis 2000 version 4.5A)
2) Expand the region of interests (typically between −20 and +5° C.)
3) Click on "Integrate Peak Linear"
4) Double-click before and after the thermal peak to insert two cursors that determine the integration limits
5) Right-click in between the two cursors and click on "accept limits"
6) The software calculates $\Delta H_{f,sample}$ in J/g Determination of $\Delta H_{f,H2O}$ Instead of using the standard value of 333.55 J/g as $\Delta H_{f,H2O}$, one can calculate $\Delta H_{f,H2O}$ for the instrument used (the value should be comprised between 333.55±30 J/g).

Three samples of 1-2 mg of deionized water (such as MilliQ grade, 18.2 MΩ cm) each are precisely weighted in a DSC steel pan (take note of the precise weight) and placed in a DSC. All samples are analyzed using the same procedure used to determine $\Delta H_{f,sample}$ described. Once determined $\Delta H_{f,sample}$, $\Delta H_{f,H2O}$, one can calculate the FWC.

Weight-Average Molecular Weight Test Method

Weight-average molecular weight values are determined using high performance liquid chromatography (HPLC) instrument system with a refractive index detector, such as the Waters Alliance 2695 system equipped with autosampler and Waters 2414 refractive index detector (Waters Inc., Milford, Mass., USA). Data storage and analysis are performed with Astra 6.1.6 software (Wyatt Technologies, Santa Barbara, Calif., USA). The chromatographic conditions used are as specified in the table below:

| Parameter | Conditions |
|---|---|
| Column Set | Guard Column - TSK Gel Guard HXL-H in-line with Three TOSOH columns: TSK Gel G4000HXL Catalog #0016137; TSK Gel G5000HXL Catalog #0016138; TSK Gel G6000HXL Catalog #0016139; |
| Mobile Phase | Tetrahydrofuran (THF) |
| Flow Rate | 1 mL/min |
| Column Temperature | 25° C. |
| Injection Volume | 100 μL |
| Detector Temperature | 35° C. |

In carrying out the calculations, the results are calibrated using a set of 12 polystyrene reference samples, such as the EasiVial PS-M set (Agilent Technologies, Santa Clara, Calif.) having known molecular weights ranging from 162 to 364,000 $M_p$ and using a second order fit. The molecular weight analyses are determined using a tetrahydrofuran (THF) mobile phase. The table below shows the molecular weights and the retention times of the polystyrene standards:

| Standard Number | Average Reported Mp | Retention Time (min) |
|---|---|---|
| 1 | 364,000 | 21.75 |
| 2 | 195,300 | 23.02 |
| 3 | 110,500 | 24.18 |
| 4 | 49,010 | 25.78 |
| 5 | 30,230 | 26.61 |
| 6 | 12,980 | 27.90 |
| 7 | 7,640 | 28.60 |
| 8 | 2,970 | 29.71 |
| 9 | 1,150 | 30.79 |
| 10 | 855 | 31.10 |
| 11 | 370 | 31.91 |
| 12 | 162 | 32.95 |

Grafting and Ratio of Polyalkylene Glycol:Vinyl Acetate Moieties Test Methods

The percent grafting is determined by 13C-NMR using a Bruker 600 MHz NMR. An inverse-gated 300 pulse sequence was used, with 16,000 scans and relaxation delay of 5 sec. Samples are prepared at 50 mg/ml in deuterated DMSO-d6 with addition of 0.79 mg/ml Gd(NO$_3$)$_3$ and 0.31 mg/ml Inositol as a Paramagnetic Relaxation Reagent. The ratio of the integration of the area between 76.75-77.5 ppm for the graft methine carbon and the integration of the area between 70.00-70.65 ppm for the PEG carbons is calculated and converted to a percent.

The weight percents for Polyalkylene Glycol:Vinyl Acetate Moieties are calculated by averaging the integration of the area of the NMR proton spectra between 1.35-2.07 ppm & 4.65-5.1 ppm for polyvinyl acetate and 3.38-3.58 ppm for Polyalkylene Glycol. The integrations are divided to find a molar ratio, and then multiplied by their respective molar mass to calculate the weight percents.

Method of Measuring Viscosity

Viscosity is measured using a HAAKE MARS from Thermo Scientific using a 60 mm 1 Cone and a gap size of 52 micrometers. The shear viscosity at 20 s$^{-1}$ can be obtained from a logarithmic shear rate sweep from 0.01 s$^{-1}$ to 1200 s$^{-1}$ at 21° C. The viscosity is expressed as centipoise (cP).

EXAMPLES

The following are non-limiting examples of the present invention.

Premixing Graft Co-Polymer and Benefit Agent Vs. Adding Separately

The following compares a process of the present invention, wherein a graft co-polymer and benefit agent are premixed and then the premix is added to consumer product adjunct material(s) to form a consumer product composition, to a conventional process, wherein a graft co-polymer and benefit agent are added separately to consumer product adjunct material(s) to form a consumer product composition. In the following Example and Comparative Example, Rhodamine 110 is utilized as a tagging agent to detect the components of the composition in images generated via Confocal Laser Scanning Fluorescence Microscopy (CLSM). The graft co-polymer utilized in the following is a polyethylene glycol-graft-polyvinyl acetate ("PEG-g-PVAc") amphiliphic co-polymer having a PEG:VAc weight ratio of 40:60, a PEG graft length of about 6,000 Daltons, and a weight-average molecular weight of about 27,000 Daltons.

Conventional Process (Comparative Example)

A comparative consumer product composition is prepared utilizing a conventional process wherein a graft co-polymer and a perfume oil benefit agent are separately added to consumer product adjunct materials to form the comparative consumer product composition.

2 grams of Hexarose (a neat perfume oil) and 5 milligrams of Rhodamine 110 are added to 98 grams of ARIEL® Original Washing Liquid laundry detergent. This mixture is stirred with a Stuart SA8 vortex mixer (Bibby Scientific, Staffordshire, UK) at 1500 rpm until the mixture is homogeneous. 5 grams of PEG-g-PVAc co-polymer are added to 95 grams of the stirred mixture. This mixture is heated to 60° C. and stirred with a Stuart SA8 vortex mixer at 1500 rpm until homogeneous. This stirred mixture is kept in an orbital shaker at 500 rpm for 1 hour at room temperature to form the comparative consumer product composition. The resulting comparative consumer product composition has approximately 60%, by weight, of water and a Free Water Content of approximately 36%.

8-12 droplets of the comparative consumer product composition (100-200 milligrams) are put in a chambered coverglass (Nunc® Lab-Tek® II chambered coverglass, 8 wells, polystyrene chambers, 1.5 borosilicate coverglass, 0.7 cm$^2$/well, 96/cs) and imaged using Confocal Laser Scanning Fluorescence Microscopy (CLSM).

FIG. 1 is a photomicrograph produced using CLSM showing that the perfume oil/tagging agent (represented by the light gray areas of the image) is outside of the graft co-polymer particles (represented by the black areas of the image) in the comparative consumer product composition.

Process of the Present Invention (Example)

A consumer product composition of the present invention is prepared utilizing a process of the present invention wherein a graft co-polymer and a perfume oil benefit agent are premixed and then the premix is added to consumer product adjunct materials to form the consumer product composition.

5 grams of PEG-g-PVAc co-polymer is added to 2 grams of Hexarose (a neat perfume oil) and 5 milligrams of Rhodamine 110. This mixture is heated to 60° C. and stirred with a Stuart SA8 vortex mixer at 1500 rpm until homogeneous. 5 grams of this stirred premix is added to 95 grams of ARIEL® Original Washing Liquid laundry detergent. This mixture is heated to 60° C. and stirred with a Stuart SA8 vortex mixer at 1500 rpm until homogeneous. This stirred mixture is kept in an orbital shaker at 500 rpm for 1 hour at room temperature to form a consumer product composition of the present invention. The resulting consumer product composition has approximately 60%, by weight, of water and a Free Water Content of approximately 36%.

8-12 droplets of the consumer product composition of the present invention (100-200 milligrams) are put in a chambered coverglass (Nunc® Lab-Tek® II chambered coverglass, 8 wells, polystyrene chambers, 1.5 borosilicate coverglass, 0.7 cm$^2$/well, 96/cs) and imaged using Confocal Laser Scanning Fluorescence Microscopy (CLSM).

FIG. 2 is a photomicrograph produced using CLSM showing that the perfume oil/tagging agent (represented by the light gray areas of the image) is inside the graft co-polymer particles of the consumer product composition of the present invention.

FIGS. 1 and 2 illustrate that compositions made by the processes of the present invention (e.g. wherein the graft co-polymer and benefit agent are premixed and then added to adjunct materials to form the compositions) provide benefit agent delivery particles which comprise the graft co-polymer and benefit agent in the compositions, whereas conventional processes not of the present invention (e.g. wherein the graft co-polymer and benefit agent are added separately to adjunct materials to form the compositions) do not provide benefit agent delivery particles which comprise the graft co-polymer and benefit agent in the compositions.

This comparison further demonstrates that a composition resulting from a process of the present invention is significantly different from a composition resulting from a conventional process, as shown in comparing the compositions as illustrated in FIGS. 1 vs. 2.

Purification of Sokalan HP-22 (for Utilization in Examples Below)

Sokalan HP-22 (BASF) is a 22% solution of Poly(ethylene oxide-g-vinyl acetate) in water. To evaluate this material, the polymer solution is first placed into a 1000 MWCO dialysis tube (SpectaPor). The sample is then dialyzed against RO water with water flow held such that complete water replacement occurs every 2 hours for a total of 48 hours of dialysis. The sample is then lyophilized using a Labconco lyophilizer.

PEG-g-PVAc: General Synthetic Procedure
(Examples 1-10)

(See Table 1 Below for Specific Amounts)

A reaction vessel with stirrer and reflux condenser is charged with the initial PEG under a nitrogen atmosphere and melted at the reaction temperature. After addition of the initial charges of vinyl acetate (freshly distilled) and t-butyl peroxypivalate initiator (dissolved in the initial dipropylene glycol), the contents are stirred for 5 minutes. To the vessel, simultaneously with constant flow rate, is metered the vinyl acetate feed (freshly distilled) over 6 hours, and t-butyl peroxypivalate initiator feed 1 (dissolved in dipropylene glycol) over 7 hours. The internal temperature is maintained at the reaction temperature with stirring throughout. After initiator feed 1 is finished the mixture is stirred at the reaction temperature for 1 hour. Then at the reaction temperature, t-butyl peroxypivalate initiator feed 2 (dissolved in dipropylene glycol) is added. One hour later t-butyl peroxypivalate initiator feed 3 (dissolved in dipropylene glycol) is added. The reaction is stirred at the reaction temperature for 4 hours.

The reaction mixture is vacuum distilled at 90° C. to remove residual vinyl acetate.

TABLE 1

Reagent quantities-Examples 1-10

| | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|
| Initial PEG charge (grams) | 22.1 | 22.5 | 22.5 | 22.5 | 64.17 | 64.17 | 64.17 | 64.17 | 22.5 | 22.5 |
| PEG Mw | 6000 | 6000 | 12000 | 12000 | 12000 | 12000 | 6000 | 6000 | 2000 | 2000 |
| Reaction Temperature, (° C.) | 70 | 90 | 70 | 90 | 70 | 90 | 70 | 90 | 70 | 90 |
| Initial vinyl acetate charge (grams) | 1.69 | 1.69 | 1.69 | 1.69 | 7.47 | 7.47 | 7.47 | 7.47 | 1.69 | 1.69 |
| Initial initiator charge (grams) | 0.02 | 0.02 | 0.02 | 0.02 | 0.058 | 0.058 | 0.058 | 0.058 | 0.02 | 0.02 |
| Initial dipropylene glycol charge (grams) | 0.061 | 0.061 | 0.061 | 0.061 | 0.174 | 0.174 | 0.174 | 0.174 | 0.061 | 0.061 |
| Vinyl acetate feed (grams) | 50 | 50 | 50 | 50 | 21.3 | 21.3 | 21.3 | 21.3 | 50 | 50 |
| Initiator feed 1 (grams) | 0.409 | 0.409 | 0.409 | 0.409 | 0.409 | 0.409 | 0.409 | 0.409 | 0.409 | 0.409 |
| Dipropylene glycol for initiator feed 1 (grams) | 1.23 | 1.23 | 1.23 | 1.23 | 1.23 | 1.23 | 1.23 | 1.23 | 1.23 | 1.23 |
| Initiator feed 2 (grams) | 0.475 | 0.475 | 0.475 | 0.475 | 0.475 | 0.475 | 0.475 | 0.475 | 0.475 | 0.475 |
| Dipropylene glycol for initiator feed 2 (grams) | 1.425 | 1.425 | 1.425 | 1.425 | 1.425 | 1.425 | 1.425 | 1.425 | 1.425 | 1.425 |

TABLE 1-continued

Reagent quantities-Examples 1-10

| | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|
| Initiator feed 3 (grams) | 0.475 | 0.475 | 0.475 | 0.475 | 0.475 | 0.475 | 0.475 | 0.475 | 0.475 | 0.475 |
| Dipropylene glycol for initiator feed 3 (grams) | 1.425 | 1.425 | 1.425 | 1.425 | 1.425 | 1.425 | 1.425 | 1.425 | 1.425 | 1.425 |

TABLE 2

Polymer Characterization of Polymers 1-10

| Sample | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|
| Mn (kDa) | 5.0 | 5.8 | 6.0 | 5.7 | 3.8 | 3.9 | 3.6 | 3.6 | 4.0 | 4.3 |
| Mp (kDa) | 12.0 | 11.9 | 20.5 | 22.4 | 6.5 | 6.3 | 6.3 | 6.0 | 6.9 | 6.5 |
| Mw (kDa) | 10.3 | 11.05 | 13.05 | 14.65 | 5.95 | 6.2 | 5.7 | 5.6 | 7.7 | 10.2 |
| PDI | 2.1 | 1.9 | 2.3 | 2.6 | 1.6 | 1.6 | 1.6 | 1.6 | 1.9 | 2.4 |
| wt % PEO | 29 | 31 | 34 | 30 | 70 | 72 | 72 | 79 | 30 | 30 |
| wt % PVAc | 71 | 69 | 66 | 70 | 30 | 28 | 28 | 21 | 70 | 70 |
| % PEO units grafted | 0.80% | 4.41% | 2.55% | 0.21% | 0.28% | 1.26% | 0.52% | 0.80% | 3.75% | 5.83% |
| Surface Energy: Nonpolar (mJ/m²) | 40.6 | 35.8 | 35.5 | 33.1 | 41.6 | 43.0 | 44.0 | 41.0 | 40.3 | 37.1 |
| Surface Energy: Polar (mJ/m²) | 8.7 | 2.7 | 1.3 | 0.5 | 21.5 | 21.1 | 17.2 | 17.2 | 3.9 | 0.1 |
| Surface Energy: Total (mJ/m²) | 49.3 | 38.5 | 36.8 | 33.6 | 63.1 | 64.0 | 61.2 | 58.2 | 44.2 | 37.2 |

Preparation of Particles Comprising a Graft Copolymer and a Benefit Agent

1. Materials
   PEG-g-PVAc, amphiphilic graft copolymer, as per Example 1-10
   Liquid detergent
   Stuart SA8 vortex mixer (Bibby Scientific, Staffordshire, UK)
   EchoTherm™ Orbital Mixing (Torrey Pines scientific, INC)
2. Procedure 2.1 Preparing a Matrix Containing an Active Substance Weigh about 5 g of graft co-polymer (Examples 1-10 in Table 1) into a glass vial and screw the cap on. Set the EchoTherm™ block heater at 80° C. and wait until the polymer is melted. Place the vial on a balance and add one of the actives to be encapsulated e.g. hueing dye, enzyme solution, non-ionics, silicones, brightener solutions or combinations thereof. Mix with a Stuart SA8 vortex mixer (Bibby Scientific, Staffordshire, UK) at 2500 rpm until a homogeneous viscous liquid is obtained. The weight ratio is intended as the total weight of the benefits agent divided the total weight of the co-polymer.

2.2 Preparing Graft Copolymer Capsules

Take an adequate amount of sample from the vial of the mixed material prepared as in 2.1 and add to another vial containing the main product formulation e.g. Liquid Detergent such as Ariel so to have a 5% w/w concentration in the detergent. Mix with a Stuart SA8 vortex mixer at 600 rpm to disperse the graft copolymer mixed with the benefit agent in the detergent matrix.

Addition of Benefit Agent Particles to Different Compositions

Upon addition, we observe the compositions under confocal microscope to assess the presence of the particles.

| | | | Formulation | | | |
|---|---|---|---|---|---|---|
| Material | Nonpolar Surface Energy/mJ/m2 | Polar Surface Energy Component/mJ/m2 | Fabric Enhancer Formulation 1 Free Water Content is 89% | Fabric Enhancer Formulation 1 with added citric acid and nonionic Free water content is 66% | Skin Care Formulation 1 Free water content is 61% | Hair Care Formulation 1 Free water content is 86% |
| Perfume + polymer according to Ex. 4 | 33.1 | 0.5 | Visible particles | Visible particles | Visible particles | Visible particles |
| Perfume + polymer according to Ex. 1 | 40.6 | 8.7 | No visible particles | Visible particles | No visible particles | No visible particles |
| Comparative Polymer | | | No visible particles | No visible particles | No visible particles | No visible particles |

|  |  |  | Formulation | | | |
| --- | --- | --- | --- | --- | --- | --- |
| Material | Nonpolar Surface Energy/mJ/m2 | Polar Surface Energy Component/mJ/m2 | Liquid Detergent Formulation 1 Free water content is 10% | Liquid Detergent Formulation 2 Free water content is 38% | Liquid Detergent Formulation 3 Free water content is 69% (Na LAS* 0%) | Liquid Detergent Formulation 4 Free water content is 67% (Na LAS* 3.5%) |
| Perfume + polymer according to Ex. 4 | 33.1 | 0.5 | Visible particles | Visible particles | Visible particles | |
| Hueing dye + polymer according to Ex. 1 | 40.6 | 8.7 | Visible particles | Visible particles | No visible particles | Visible particles (multi-core) FIG. 2 |
| Perfume + polymer according to Ex. 1 | 40.6 | 8.7 | Visible particles | Visible particles | No visible particles | Visible particles (multi-core) FIG. 2 |
| Perfume + polymer according to Ex. 6 | 43.1 | 21.0 | Visible particles | No visible particles | No visible particles | |
| Comparative Polymer - PVOH | | | No visible particles | No visible particles | No visible particles | |

| Objective | Particle Architecture | Polymer | Benefit Agent | level in Polymer | Matrix or FP | % Free water | self assembled |
| --- | --- | --- | --- | --- | --- | --- | --- |
| form polymer capsules, nil benefit agent | Matrix-like | Graft co-polymer of 40% PEG6000 and 60% PVAc, Mw 27K | none | 0 | Liquid Detergent Formulation 1 | 10% | yes |
| | Matrix-like | Sokalan PG101** | None | 0 | Liquid Detergent Formulation 1 | 10% | yes |
| | Multi-core | Graft co-polymer of 40% PEG6000 and 60% PVAc, Mw 27K | None | 0 | Liquid Detergent Formulation 2 | 38% | yes |
| | Multi-core | Sokalan PG101** | None | 0 | Liquid Detergent Formulation 2 | 38% | yes |
| | Matrix-like | Sokalan HP22 *** | None | 0 | Liquid Detergent Formulation 1 | 10% | yes |
| | Matrix-like | Ex. 1 | None | 0 | Liquid Detergent Formulation 1 | 10% | yes |
| | Matrix-like | Ex. 2 | None | 0 | Liquid Detergent Formulation 1 | 10% | yes |
| | Matrix-like | Ex. 3 | None | 0 | Liquid Detergent Formulation 1 | 10% | yes |
| | Matrix-like | Ex. 4 | None | 0 | Liquid Detergent Formulation 1 | 10% | yes |
| | Matrix-like | Ex. 5 | None | 0 | Liquid Detergent Formulation 1 | 10% | yes, marginal |
| | Matrix-like | Ex. 6 | None | 0 | Liquid Detergent Formulation 1 | 10% | yes, marginal |
| | Matrix-like | Ex. 7 | None | 0 | Liquid Detergent Formulation 1 | 10% | yes, marginal |
| | Matrix-like | Ex. 8 | None | 0 | Liquid Detergent Formulation 1 | 10% | yes, marginal |
| | Nothing | Graft co-polymer of 40% PEG6000 and 60% PVAc, Mw 27K | None | 0 | Liquid Detergent Formulation 3 | 69% | no |
| | Matrix-like | Ex. 3 | None | 0 | Liquid Detergent Formulation 3 | 69% | yes |
| | Matrix-like | Sokalan PG101** | None | 0 | L'Oreal Shampoo | 77% | Yes |
| | Multicore | Ex. 4 | None | 0 | Olaz Wrinkle | 61% | yes |
| | Matrix-like | Ex. 4 | None | 0 | Pantene Conditioner | 86% | yes |
| Perfume | Matrix-like | Sokalan PG101** | Hexarose | 20% | Liquid Detergent Formulation 1 | 10% | yes |
| | Matrix-like | Ex. 4 | Perfume Oil | 20, 40, 60, 80% | Fabric Enhancer Formulation 1 | 89% | yes |
| Silicone | Matrix-like | Sokalan PG101** | Silfoam SD168 (Wacker) | | Liquid Detergent Formulation | 40% | Yes |

*Na LAS sodium alkyl benzene sulfonate with a chain length $C_{11-13}$
**Supplied ex BASF, Mixture of 70% Graft co-polymer of 40% PEG6000 and 60% PVAc, Mw 27K, 20% Lutensol XL100 (BASF), 7% water and 3% tripropylene glycol
*** Supplied ex BASF, Graft co-polymer of 40% PEG6000 and 60% PVAc The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process of making a feedstock composition comprising benefit agent delivery particles, said process comprising the steps of:
    combining a graft co-polymer and a benefit agent to form a premix composition,
        wherein said graft co-polymer is a co-polymer of polyalkylene glycol and vinyl acetate that comprises a polyalkylene glycol backbone comprising vinyl acetate moieties that are covalently attached to said polyalkylene glycol backbone,
        wherein said benefit agent comprises perfume oil, and
    combining said premix composition and water to form said feedstock composition,
    wherein said feedstock composition comprises less than about 98%, by weight of the feedstock composition, of water; and
    wherein said benefit agent delivery particles comprise said graft co-polymer and said benefit agent.

2. A process according to claim 1, wherein said feedstock composition comprises from about 1% to about 98%, by weight of the feedstock composition, of water.

3. A process according to claim 1, wherein said feedstock composition has a Free Water Content of less than about 96%.

4. A process according to claim 1, wherein said feedstock composition is substantially free of consumer product adjunct material, wherein the consumer product adjunct material is selected from the group consisting of surfactants, waxes, hydrocarbons, higher fatty acids, essential oils, lipids, skin coolants, vitamins, sunscreens, antioxidants, glycerine, catalysts, silicon dioxide particles, odor-controlling materials, chelating agents, antistatic agents, softening agents, insect and moth repelling agents, colorants, germ control agents, mold control agents, antiviral agents, drying agents, stain resistance agents, soil release agents, dye fixatives, dye transfer inhibitors, optical brighteners, anti-allergenic agents, water-proofing agents, skin care agents, aloe vera, vitamin E, shea butter, cocoa butter, antiperspirant actives, cationic polymers, emollients, non-steroidal anti-inflammatory agents, topical anesthetics, artificial tanning agents, sebum inhibitors, protease inhibitors, desquamation enzyme enhancers, anti-glycation agents, and mixtures thereof.

5. A process of making a consumer product composition comprising benefit agent delivery particles, said process comprising the steps of:
    combining a feedstock composition produced according to the process of claim 1 and consumer product adjunct material to form said consumer product composition.

6. A process of making a consumer product composition comprising benefit agent delivery particles, said process comprising the steps of:
    combining a graft co-polymer and a benefit agent to form a premix composition,
        wherein said graft co-polymer is a co-polymer of polyalkylene glycol and vinyl acetate that comprises a polyalkylene glycol backbone comprising vinyl acetate moieties that are covalently attached to said polyalkylene glycol backbone,
        wherein said benefit agent comprises perfume oil, and
    combining said premix composition and consumer product adjunct material to form said consumer product composition.

7. A process according to claim 6, wherein said consumer product adjunct material is selected from the group consisting of perfume raw materials, silicone oils, waxes, hydrocarbons, higher fatty acids, essential oils, lipids, skin coolants, vitamins, sunscreens, antioxidants, glycerine, catalysts, bleach particles, silicon dioxide particles, odor-controlling materials, chelating agents, antistatic agents, softening agents, insect and moth repelling agents, colorants, germ control agents, mold control agents, antiviral agents, drying agents, stain resistance agents, soil release agents, dye fixatives, dye transfer inhibitors, optical brighteners, anti-abrasion agents, wear resistance agents, anti-foaming agents, anti-allergenic agents, enzymes, water-proofing agents, skin care agents, aloe vera, shea butter, cocoa butter, antiperspirant actives, cationic polymers, hueing dyes, emollients, non-steroidal anti-inflammatory agents, topical anesthetics, artificial tanning agents, sebum inhibitors, protease inhibitors, desquamation enzyme enhancers, anti-glycation agents, and mixtures thereof.

8. A process according to claim 6, wherein said consumer product composition comprises from about 1% to about 98%, by weight of the consumer product composition, of water.

9. A process according to claim 6, wherein said consumer product composition has a Free Water Content of less than about 96%.

10. A process according to claim 6, wherein said step of combining said graft co-polymer and said benefit agent further comprises heating said graft co-polymer to a temperature above a melting point of said graft co-polymer.

11. A process according to claim 6, wherein said step of combining said graft co-polymer and said benefit agent further comprises heating said graft co-polymer to at least 45° C.

12. A process according to claim 6, wherein said step of combining said graft co-polymer and said benefit agent comprises mixing said graft co-polymer and said benefit agent in a mixing device at a rate of from about 500 to about 3000 rpm.

13. A process according to claim 6, wherein said benefit agent further comprises a member selected from the group consisting of enzymes, bleaching agents, silicones, hueing agents, and mixtures thereof.

14. A process according to claim 6, wherein said co-polymer of polyalkylene glycol and vinyl acetate has:
   (i) a weight-average molecular weight of from about 2000 Daltons to about 250,000 Daltons, and
   (ii) a ratio of polyalkylene glycol to vinyl acetate moieties of from about 5:1 to about 1:10.

15. A process according to claim 6, wherein said co-polymer of polyalkylene glycol and vinyl acetate has from 1 to about 10 vinyl acetate grafts per polyalkylene glycol backbone.

16. A process according to claim 6, wherein said graft co-polymer further comprises at least one monomer selected from the group consisting of vinyl esters, alkyl acrylates, alkyl methacrylates, alkyl acrylamides, alkyl methacrylamides, styrenes, halogenated olefins, and mixtures thereof.

17. A process according to claim 6, wherein said benefit agent delivery particles have an intensity-averaged hydrodynamic diameter of from about 10 to about 100 nanometers.

18. A process according to claim 6, wherein said consumer product adjunct material comprises surfactant at a level of from about 0.1% to about 25%, by weight of said composition.

19. A process according to claim 18, wherein said surfactant is selected from the group consisting of cationic surfactant, anionic surfactant, nonionic surfactant, and mixtures thereof.

20. A process according to claim 19, wherein said surfactant is cationic surfactant.

21. A process according to claim 19, wherein said surfactant is nonionic surfactant.

22. A process of making a consumer product composition comprising benefit agent delivery particles, said process comprising the steps of:
   combining a graft co-polymer and a benefit agent to form a premix composition,
      wherein said graft co-polymer is a co-polymer of polyalkylene glycol and vinyl acetate having:
         (i) a weight-average molecular weight of from about 2000 Daltons to about 250,000 Daltons, and
         (ii) a ratio of polyalkylene glycol to vinyl acetate moieties of from about 5:1 to about 1:10,
      wherein said benefit agent comprises perfume oil, and
   combining said premix composition and consumer product adjunct material to form said consumer product composition.

23. A process of making a consumer product composition comprising benefit agent delivery particles, said process comprising the steps of:
   combining a graft co-polymer and a benefit agent to form a premix composition,
      wherein said graft co-polymer is a co-polymer of polyalkylene glycol and vinyl acetate having from 1 to about 10 vinyl acetate grafts per polyalkylene glycol backbone,
      wherein said benefit agent comprises perfume oil, and
   combining said premix composition and consumer product adjunct material to form said consumer product composition.

24. A feedstock composition produced according to the process of claim 1.

25. A feedstock composition according to claim 24, wherein said feedstock composition comprises benefit agent delivery particles comprising graft co-polymer and benefit agent.

26. A consumer product composition produced according to the process of claim 5.

27. A consumer product composition according to claim 26, wherein said consumer product composition comprises benefit agent delivery particles comprising graft co-polymer and benefit agent.

28. A consumer product composition produced according to the process of claim 6.

29. A consumer product composition according to claim 28, wherein said consumer product composition comprises benefit agent delivery particles comprising graft co-polymer and benefit agent.

* * * * *